(12) United States Patent
Vacca

(10) Patent No.: US 10,488,343 B2
(45) Date of Patent: *Nov. 26, 2019

(54) METHODS AND APPARATUSES FOR LABEL-FREE PARTICLE ANALYSIS

(71) Applicant: Kinetic River Corp., Mountain View, CA (US)

(72) Inventor: Giacomo Vacca, Campbell, CA (US)

(73) Assignee: Kinetic River Corp., Mountain View, CA (US)

( * ) Notice: Subject to any disclaimer, the term of this patent is extended or adjusted under 35 U.S.C. 154(b) by 146 days.

This patent is subject to a terminal disclaimer.

(21) Appl. No.: 15/723,088

(22) Filed: Oct. 2, 2017

(65) Prior Publication Data

US 2018/0299383 A1    Oct. 18, 2018

Related U.S. Application Data

(63) Continuation of application No. 14/461,293, filed on Aug. 15, 2014, now Pat. No. 9,778,193.

(60) Provisional application No. 61/869,035, filed on Aug. 22, 2013.

(51) Int. Cl.
| *G01N 15/00* | (2006.01) |
| *G01N 21/65* | (2006.01) |
| *G01N 15/14* | (2006.01) |
| *G01N 15/10* | (2006.01) |

(52) U.S. Cl.
CPC ......... *G01N 21/65* (2013.01); *G01N 15/1434* (2013.01); *G01N 15/1459* (2013.01); *G01N 2015/1006* (2013.01); *G01N 2015/1438* (2013.01); *G01N 2021/653* (2013.01); *G01N 2201/0697* (2013.01); *G01N 2201/06113* (2013.01)

(58) Field of Classification Search
CPC ............... G01N 21/65; G01N 15/1434; G01N 15/1459; G01J 3/02; G01J 3/44
See application file for complete search history.

(56) References Cited

U.S. PATENT DOCUMENTS

| 2003/0160955 | A1 | 8/2003 | Xie et al. |
| 2010/0118292 | A1 | 5/2010 | Park et al. |
| 2016/0178439 | A1 | 6/2016 | Freudiger et al. |

OTHER PUBLICATIONS

Knutsen et al. "Chirped coherent anti-Stokes Raman scattering for high spectral resolution spectroscopy and chemically selective imaging," The Journal of Physical Chemistry B 110.12 (2006): 5854-5864.
Camp Jr. et al. "Multiplex coherent anti-Strokes scattering (MCARS) for chemically sensitive, label-free flow cytometry," Optics Express vol. 17, No. 25 (Dec. 7, 2009), pp. 22879-22889.
Wang et al. "Microfluidic CARS cytometry," Optics Express vol. 16, No. 8 (Apr. 14, 2008), pp. 5782-5789.

*Primary Examiner* — Rebecca C Bryant
(74) *Attorney, Agent, or Firm* — Aurora Consulting LLC; Ashley Sloat

(57) ABSTRACT

An apparatus to provide a label-free or native particle analysis comprises a light generating system producing first light pulses at a first wavelength and second light pulses at a second wavelength; and a flow cell coupled to the light generating system to convey particles for analysis. The light generating system is configured to chirp at least one of the first light pulses and the second light pulses to analyze the particles.

20 Claims, 11 Drawing Sheets

METHODS AND APPARATUSES FOR LABEL-FREE PARTICLE ANALYSIS

This application claims priority to U.S. Nonprovisional patent application Ser. No. 14/461,293, entitled "METHODS AND APPARATUSES FOR LABEL-FREE PARTICLE ANALYSIS," filed Aug. 5, 2014 and issued on Oct. 3, 2017 as U.S. Pat. No. 9,778,193, which claims the benefit of U.S. Provisional Patent Application No. 61/869,035, entitled "METHODS AND APPARATUSES FOR LABEL-FREE PARTICLE ANALYSIS," filed on Aug. 22, 2013, both of which are incorporated herein by reference in their entirety.

FIELD

Embodiments as described herein relate to analysis of particles, specifically to rapid, label-free analysis of particles.

BACKGROUND

Generally, the rapid, accurate, sensitive, and specific analysis of microscopic elements such as cells, microbes, and particulates (hereafter, "particles") is of great importance in cell biology research, pharmaceutical research and development, microbiology, hematological diagnostics, water and milk quality testing, paint and emulsion production, and other applications. Historically, inspection and characterization of particles were carried out on optical microscopes, which are still in widespread use in medical, research, and industrial laboratories worldwide. However, even as microscopes have become increasingly sophisticated, with functions such as, e.g., fluorescence detection, confocal geometry, and superresolution, they continue to be severely limited in analysis speed and sample throughput. Collection of image information at high enough resolution to allow characterization and identification of human cells is certainly possible, but at a steep price in terms of the total number of individual particles that can be so analyzed in any reasonable amount of time.

For the last several decades, an alternative modality of analysis, characterization, and counting of particles has emerged and taken root-flow cytometry. This technology contrasts with microscopy in a couple of key ways: it works by flowing a liquid sample across a single fixed point of interrogation, rather than interrogating (whether by scanning or imaging) over a fixed sample; and it generally analyzes information averaged over each entire particle, rather than resolving details at, e.g., a subcellular or even subnuclear level. The result is a trade-off between spatial resolution and speed: microscopy excels at the former, flow cytometry at the latter. Accordingly, the two techniques have in recent years co-evolved by commanding complementary applications, often performed in the same laboratory and even side by side: For example, routine hematology diagnostics is near-universally carried out on highly efficient automated analyzers built on flow cytometric principles, but time-consuming microscope-based review of blood slides is just as universally performed to clarify by high-resolution visual inspection those instances where the flow cytometer results are inconclusive.

Generally, contemporary flow cytometric analysis relies on several established interrogation techniques to extract identifying information from each passing particle: dc electrical impedance, ac electrical conductivity, optical extinction, light scattering, and fluorescence. Dc impedance is typically very limited in the ability to distinguish cells similar in volume but different in composition; it is therefore generally used only for first-line hematological screening, or as add-on to optical methods on advanced analyzers. Ac electrical conductivity and optical extinction can each add a dimension of differentiation to help distinguish similar cells, but not in isolation. Typically, the workhorses of flow cytometry are (elastic) light scattering and fluorescence.

Generally, scattering depends on refractive index variations either between the particle and its liquid surroundings, or within the particle itself; it gives relatively coarse information on presence, size, and rough morphology of the particle itself and (in the case of a cell) any nucleus and/or cytoplasmic bodies present. Scattering works on intrinsic properties of particles and does not generally require the use of expensive reagents. However, it does not effectively differentiate between similarly sized and structured, but functionally distinct, particles (e.g., a lymphocyte and a nucleated erythrocyte; or two microbeads surface-functionalized with different analyte-specific antibodies).

Fluorescence is by far the optical interrogation method most widely used in flow cytometry. A fluorophore can be intrinsic (such as tryptophan); externally introduced as a standalone agent (such as propidium iodide); or externally introduced as a conjugate to a particular antibody (such as, e.g., phycoerythrin conjugated to CD4). There are further variations, such as tandem dyes and quantum dots, which while useful, may not be directly relevant here. Autofluorescence from compounds naturally or biologically stimulated within a cell are of interest in certain research areas; however, the broadest application of fluorescence in flow cytometry is based on the introduction of external fluorophores. Non-conjugated fluorophores are typically used to bind selectively to major cell constituents such as DNA or RNA, and return information on, e.g., the presence or absence of a nucleus, or on the maturation stage of certain blood cells; but they are not particularly specific. They are therefore used in combination with either scattering (in the context, e.g., of hematological diagnosis) or panels of fluorescent antibody conjugates.

Antibody-conjugated fluorophores are commonly called "tags" or "labels" in that they perform the function of selectively identifying a particle based on the presence of matching antigens on the particle surface; also used are fluorescent labels that bind to and identify intracellular elements, such as, e.g., actin or cytokeratin. As an example of antibody tagging in peripheral blood samples, leukocytes can be selectively identified out of the much vaster population of erythrocytes, in company of which they are found, by incubating the sample with a fluorophore conjugated to the CD45 antibody (which selectively binds to the matching CD45 antigen on the leukocyte surface). Flow cytometric analysis of the incubated sample results in leukocytes, but not erythrocytes, generating fluorescence upon passing through the interrogation region. Tagging by antibody conjugation and fluorescence analysis by flow cytometry has enabled great strides in the field of immunology, where cell type, function, and even stage of development are associated with the expression of distinct sets of surface antigens.

The development and manufacture of fluorescent antibody conjugates—particularly monoclonal antibodies (MAbs)—is, however, cumbersome and expensive. While some recent advances have been made in the generation of synthetic antibodies, most antibodies are produced with the use of animal-derived cells in a lengthy process. And while several long-established fluorescent dyes are relatively inexpensive, the drive in flow cytometry toward greater and greater multiplexing—i.e., the concurrent use of multiple tags, and therefore multiple fluorophores, in the same assay—has pushed the field into a great proliferation of custom, relatively expensive, fluorophore compounds. In addition, the process of conjugation itself is an additional factor in the final cost of the antibody conjugate.

Typical research assays performed on flow cytometers include ones for transfection, cell signaling, cell lineage, and stem cells; many of these assays, especially in immunology, require the concurrent use of cocktails of large numbers of fluorescent MAb conjugates, resulting in relatively high costs even for experiments with few repeats. Clinical practice is, by contrast, generally focused on the use of relatively few labels—for example, in management of AIDS patients, where only two or three separate MAbs are required for each test—but the relative frequency of such tests in a typical laboratory is much greater. In either research or clinical flow cytometry applications, therefore, expensive reagents used in selective labeling of cells or microparticles are a definite concern. Annual reagent expenditures in both research and clinical laboratories—expenditures dominated by fluorescent MAb conjugate labels—can be comparable to, and sometimes exceed, the capital cost of a flow cytometer itself, which typically has a life span of five years or more.

Additionally, there is the issue of fragility. MAbs and MAbs-based labels typically have to be kept under strict refrigeration protocols, and thawed carefully just prior to use. This means operational complexity in terms of both proper storage at or near the point of use (hospital or institution) and proper handling during the entire chain of custody from manufacturer to end user. In developed countries this complexity is manageable but drives up the cost assays using MAb reagents; in developing countries it often means that those assays cannot be performed. In resource-poor countries, power shortages, unreliable distribution networks, and limited means of refrigeration, not to mention more general financial constraints, make use of MAb-conjugated fluorophore labels always challenging and often impossible.

Also, whether dealing with MAb tags or with non-conjugated fluorophores, every assay requiring labels involves at least one, and frequently more, incubation steps. Incubation conditions like temperature and time vary considerably, but it is common for a single surface-antigen MAb incubation step to take 15 minutes. This delay in the workflow is significant for a laboratory performing routine tests, and—together with the high cost of MAbs—has limited widespread adoption of MAb assays for clinical use to those that currently cannot be reliably performed any other way, like the CD4-positive T-lymphocyte test for AIDS patients.

Moreover, the tolerance toward difficult and time-consuming sample preparation steps may be relatively high in the context of a clinical laboratory, and very high in a research laboratory, but it is generally extremely low in industrial, or industrial-scale, process monitoring steps, where throughput-limiting (and costly) bottlenecks can mean the difference between economically viable and non-viable production. Such, for example, is the case of milk quality testing, currently performed mainly in central reference laboratories equipped with high-throughput flow cytometric instruments. Testing for water quality has similar constraints. In both cases both a high throughput and a low cost per assay are operational imperatives.

In the field of microscopy, certain advances in the use of spectroscopy have made it possible to analyze specimens without the need for expensive reagents like MAb-conjugated fluorophore labels. Spectroscopy generally provides detailed information about the intrinsic chemical composition of a sample by interrogating the sample with optical radiation. Absorption spectroscopy in its various forms can be very sensitive, but it is not well suited to water-rich samples and aqueous solutions and suspensions. In such cases, inelastic scattering spectroscopy techniques are more effective. These techniques differ from conventional (elastic) light scattering as commonly used in flow cytometry in that they rely on inelastic light scattering—i.e., based on the transfer of energy from the interrogating photons to the material under analysis or vice versa. Raman scattering, resonant Raman scattering, and Coherent Anti-Stokes Raman Scattering (CARS) are examples of such techniques that have been successfully applied to the study of fixed specimens (as on microscope slides) or, more recently, in vivo with small animals. In CARS, pulses at two different optical frequencies ($\nu_{pump}$ and $\nu_{Stokes}$) are combined at the sample; the nonlinear optical interaction that results from the high peak powers (due to the short pulse duration) is responsible for the CARS signal at a third optical frequency ($\nu_{anti-Stokes}=2\nu_{pump}-\nu_{Stokes}$). In particular, variations on the CARS technique, such as forward CARS (F-CARS); epi-CARS; polarized CARS (P-CARS); multiplex CARS (M-CARS); broadband CARS (B-CARS) and closely related approaches, such as Stimulated Raman Scattering (SRS), have all been demonstrated in biomicroscopy applications. Each of these techniques is an improvement over traditional microscopy in that it provides detailed information about the chemical make-up of the sample, greatly adding specificity to the analysis.

However, despite advances that enable real-time video-rate analysis of a specimen, all of these techniques are far too slow, by several orders of magnitude, to compete with flow cytometry in the sheer number of cells or other particles that can be analyzed in a given unit of time. Accordingly, they have overwhelmingly been developed for investigation of stationary samples, and are therefore unsuitable for the kind of ensemble-wide cellular assays provided by flow cytometry.

There have been attempts at combining the superior chemical specificity of spectroscopy with the sample interrogation framework of flow cytometry. For example, experimental results in recent years demonstrated the application of particular versions of CARS spectroscopy to samples flowing in microchannels. However, these results suffered from severe limitations. In the study by Wang et al. [Wang et al., *Optics Express* 16, 5782 (2008)], schematically represented in FIG. 1(*a*), an apparatus 100 includes a mode-locked laser oscillator 110 and a mode-locked laser oscillator 120, a synchronization control module 130, a flowcell 140 containing a flow channel, and a microscope objective 102. Mode-locked laser oscillators 110 and 120 are synchronized by a control signal 101 produced by synchronization control module 130; mode-locked laser oscillator 110 generates a pump pulse train 103 at a wavelength corresponding to the desired CARS pump wavelength, and mode-locked laser oscillator 120 generates a Stokes pulse train 105 at a wavelength corresponding to the desired CARS Stokes wavelength; the pump and Stokes pulse trains are combined and focused by objective 102 onto particles for analysis in the flow channel of flowcell 140. Pulse trains 103 and 105 are both a series of pulses which interact with a particle such that multiple pulses in the train interact with the particle. None of these pulses in these trains are chirped.

In this example, the CARS analysis is restricted to a single vibrational CARS (anti-Stokes) frequency corresponding to the difference between the CARS pump frequency of pump pulse train 103 and the CARS Stokes frequency of Stokes pulse train 105. Additionally, this apparatus achieves a sample flow velocity of about 40 mm/s—almost three orders of magnitude slower than a typical commercial flow cytometer and unsuitable for laboratory-based analysis of real samples in a reasonable time.

In another example, the study by Camp Jr. et al. [Camp Jr. et al., *Optics Express* 17, 22879 (2009)] schematically represented in FIG. 1(*b*), an apparatus 150 includes a mode-locked laser oscillator 160, a photonic crystal fiber 170, a flowcell 180 containing a flow channel, and a microscope objective 152. Mode-locked laser oscillator 160 generates a pulse train 153 at a wavelength corresponding to the desired CARS pump wavelength; a portion of such pulse train is split and fed into photonic crystal fiber 170, while the rest continues as a pump pulse train 155. Photonic crystal fiber 170 generates by nonlinear optical processes a Stokes pulse train 157 with light spread across a band of wavelengths, each acting as a CARS Stokes wavelength; the pump and Stokes pulse trains are combined and focused by objective 152 onto particles for analysis in the flow channel of flowcell 180. Pulse trains 153 and 155 are both a series of pulses that interact with a particle such that multiple pulses in the train interact with the particle. None of these pulses in these trains are chirped.

In this example, broader spectral analysis (referred to as multiplex CARS, or M-CARS) than that depicted in FIG. 1(*a*) is achieved through the use of a photonic crystal fiber, a specialty optical fiber with an optical damage threshold that poses severe constraints on the peak power of the pulse train sent through it. As a result, this apparatus achieves a sample flow velocity of less than 200 μm/s—about 50,000 times slower than in conventional flow cytometers and unsuitable for laboratory-based analysis of real samples in a reasonable time. At these speeds, any benefit accruing from broadband CARS spectroscopy is nullified by the resulting impractically low sample analysis throughput.

Existing solutions for analysis of microscopic particles therefore suffer from a number of disadvantages, as follows:

dc impedance, ac impedance, optical extinction, and elastic light scattering in flow cytometry; and brightfield, darkfield, phase contrast, and other traditional optical techniques in microscopy, are not of themselves sufficiently specific to produce information with which to reliably distinguish particles of different types, particularly in many biological applications;

in flow cytometry and microscopy, use of standalone fluorophores provides limited specificity, and additionally requires incubation, which adds costs and reduces efficiency in high-throughput operations;

in flow cytometry and microscopy, use of fluorophore-conjugated monoclonal antibodies requires lengthy incubation, requires complex and expensive measures for shipment and storage of the fragile reagents, and adds significant costs to operations on a per-assay basis;

in microscopy, whether traditional or coupled with advanced spectroscopic techniques like CARS, analysis of stationary samples is much too slow to practically, efficiently, and cost-effectively provide information on a sufficient numbers of particles to confer to such analysis the required statistical significance in most applications;

in CARS spectroscopy as demonstrated to analysis of flowing samples, the current speed of analysis is much too slow for practical implementation, even when trade-offs are made in range of spectral coverage, resulting additionally in very limited compositional information.

SUMMARY

Embodiments of apparatuses and methods to provide a label-free or native particle analysis are described. In an embodiment, an apparatus comprises a light generating system producing cross-chirped pairs of first light pulses at a first wavelength and second light pulses at a second wavelength; and optional flow cell (or other chamber) coupled to the light generating system to convey or hold the particles for analysis. An optical system is coupled to the light generating system to chirp at least one of the first light pulses and the second light pulses to analyze the particles. The chamber can be similar to a microscope slide if a flow cytometer is not used in one embodiment.

In an embodiment, an apparatus comprises a light generating system producing first light pulses at a first wavelength and second light pulses at a second wavelength, the second wavelength being different from the first wavelength; and a flow cell coupled to the light generating system to convey particles for analysis. An optical system is coupled to the light generating system to chirp at least one of the first light pulses and the second light pulses to analyze the particles.

In an embodiment, an apparatus comprises a light generating system producing first light pulses at a first wavelength and second light pulses at a second wavelength; and a flow cell coupled to the light generating system to convey particles for analysis. An optical system is coupled to the light generating system to chirp at least one of the first light pulses and the second light pulses to analyze the particles. A collecting and analyzing system is coupled to the light generating system to collect and analyze light resulting from an interaction of the first light pulses and the second light pulses with the particles.

In an embodiment, an apparatus comprises a light generating system producing first light pulses at a first wavelength and second light pulses at a second wavelength; and a flow cell coupled to the light generating system to convey particles for analysis. An optical system is coupled to the light generating system to chirp at least one of the first light pulses and the second light pulses to analyze the particles. An optical module is coupled to the light generating system to combine the first light pulses and the second light pulses to deliver to the particles. The particles are each exposed to a single combined light pulse from one of the first light pulses and one of the second light pulses.

In an embodiment, an apparatus comprises a light generating system producing first light pulses at a first wavelength and second light pulses at a second wavelength; and a flow cell coupled to the light generating system to convey particles for analysis. An optical system is coupled to the light generating system to chirp at least one of the first light pulses and the second light pulses to analyze the particles. A synchronization system is coupled to the light generating system to synchronize the first light pulses and the second light pulses.

In an embodiment, an apparatus comprises a light generating system producing first light pulses at a first wavelength and second light pulses at a second wavelength; and a flow cell coupled to the light generating system to convey particles for analysis. An optical system is coupled to the light generating system to chirp at least one of the first light pulses and the second light pulses to analyze the particles. A light source is coupled to the light generating system to illuminate the particles to generate a trigger light.

In an embodiment, a particle analysis apparatus comprises a light generating system producing first light pulses at a first wavelength and second light pulses at a second wavelength.

A flow cell is coupled to the light generating system to convey a plurality of particles for analysis. A first optical system is coupled to the light generating system to generate combined light pulses from the first light pulses and the second light pulses to deliver to the particles. The particles are each exposed to one of the combined light pulses.

In an embodiment, a particle analysis apparatus comprises a light generating system producing first light pulses at a first wavelength and second light pulses at a second wavelength, the second wavelength being different from the first wavelength. A flow cell is coupled to the light generating system to convey a plurality of particles for analysis. A first optical system is coupled to the light generating system to generate combined light pulses from the first light pulses and the second light pulses to deliver to the particles. The particles are each exposed to one of the combined light pulses.

In an embodiment, a particle analysis apparatus comprises a light generating system producing first light pulses at a first wavelength and second light pulses at a second wavelength. A flow cell is coupled to the light generating system to convey a plurality of particles for analysis. A first optical system is coupled to the light generating system to generate combined light pulses from the first light pulses and the second light pulses to deliver to the particles. The particles are each exposed to one of the combined light pulses. A collecting and analyzing system is coupled to the light generating system to collect and analyze light resulting from the interaction of the combined light pulses with the particles.

In an embodiment, a particle analysis apparatus comprises a light generating system producing first light pulses at a first wavelength and second light pulses at a second wavelength. A flow cell is coupled to the light generating system to convey a plurality of particles for analysis. A first optical system is coupled to the light generating system to generate combined light pulses from the first light pulses and the second light pulses to deliver to the particles. The particles are each exposed to one of the combined light pulses. A second optical system is coupled to the light generating system to chirp at least one of the first light pulses and the second light pulses.

In an embodiment, a particle analysis apparatus comprises a light generating system producing first light pulses at a first wavelength and second light pulses at a second wavelength. A flow cell is coupled to the light generating system to convey a plurality of particles for analysis. A first optical system is coupled to the light generating system to generate combined light pulses from the first light pulses and the second light pulses to deliver to the particles. The particles are each exposed to one of the combined light pulses. A synchronization system is coupled to the light generating system to synchronize the first light pulses and the second light pulses.

In an embodiment, a particle analysis apparatus comprises a light generating system producing a first light pulse at a first wavelength and a second light pulse at a second wavelength. A flow cell coupled to the light generating system to convey a particle for analysis. A first optical system coupled to the light generating system to generate a combined light pulse from the first light pulse and the second light pulse to analyze the particle. A light source is coupled to the light generating system to illuminate the particle to generate a trigger optical beam for the combined light pulse.

In an embodiment, a particle analysis apparatus comprises a light generating system producing a first light pulse at a first wavelength and a second light pulse at a second wavelength. A flow cell coupled to the light generating system to convey a particle for analysis. A first optical system coupled to the light generating system to generate a combined light pulse from the first light pulse and the second light pulse to analyze the particle. A light source is coupled to the light generating system to illuminate the particle to generate a trigger optical beam for the combined light pulse. A second optical system coupled to the light generating system to chirp at least one of the first light pulse and the second light pulse.

In an embodiment, a particle analysis apparatus comprises a light generating system producing a first light pulse at a first wavelength and a second light pulse at a second wavelength. A flow cell coupled to the light generating system to convey a particle for analysis. A first optical system coupled to the light generating system to generate a combined light pulse from the first light pulse and the second light pulse to analyze the particle. A light source is coupled to the light generating system to illuminate the particle to generate a trigger optical beam for the combined light pulse. A collecting and analyzing system is coupled to the light generating system to collect and analyze light resulting from the interaction of the combined light pulse with the particle.

In an embodiment, first light pulses are generated at a first wavelength. Second light pulses are generated at a second wavelength. Particles are conveyed for analysis. At least one of the first light pulses and the second light pulses is chirped to analyze the particles.

In an embodiment, first light pulses at a first wavelength are generated. Second light pulses at a second wavelength are generated. Particles are conveyed for analysis. Combined light pulses are generated from the first light pulses and the second light pulses to deliver the particles. Each particle is exposed to one of the combined light pulses.

In an embodiment, a first light pulse is generated at a first wavelength. A second light pulse is generated at a second wavelength. A particle is conveyed for analysis. A combined light pulse is generated from the first light pulse and the second light pulse to analyze the particle. The particle is illuminated to generate a trigger optical beam for the combined light pulse.

In an embodiment, a first light pulse at a first wavelength and a second light pulse at a second wavelength are generated. At least one of the first light pulse and the second light pulse are chirped to analyze a particle. The first light pulse and the second light pulse are combined to generate a combined chirped pulse. The particle is interrogated using the chirped combined pulse.

In accordance with at least one embodiment, an apparatus for label-free particle or native analysis comprises a channel for flow of particles suspended in a carrier fluid, a laser system providing ultrafast amplified, synchronized, and cross-chirped pairs of light pulses, a spectrometer, a continuous-wave triggering light source, one or more light scattering photodetectors, and an electronic detector and a data processing system to collect, digitize, process, analyze, and present the signals from interactions between the laser light and particles presented for analysis.

Advantages of one or more embodiments can include a) a method and an apparatus for particle analysis that confer compositional specificity to the results on a particle-by-particle basis, enabling effective differentiation of similar particles;

b) a method and an apparatus for particle analysis without the need for incubation in sample preparation;

c) a method and an apparatus for particle analysis without the need for reagents that are expensive, require complex and costly shipment and storage procedures, and/or involve lengthy incubation steps;

d) a method and an apparatus for particle analysis that do not require the sample to be stationary;

e) a method and an apparatus for particle analysis that produce spectroscopic compositional information on a particle-by-particle basis in flowing samples, with sufficient spectral coverage, and at high enough throughput to allow sufficient statistical analysis on large ensembles of particles.

Other features and advantages of embodiments will be apparent from the accompanying drawings and from the detailed description that follows.

BRIEF DESCRIPTION OF DRAWINGS

The embodiments as described herein are illustrated by way of example and not limitation in the figures of the accompanying drawings in which like references indicate similar elements.

DETAILED DESCRIPTION

Figure 1A:
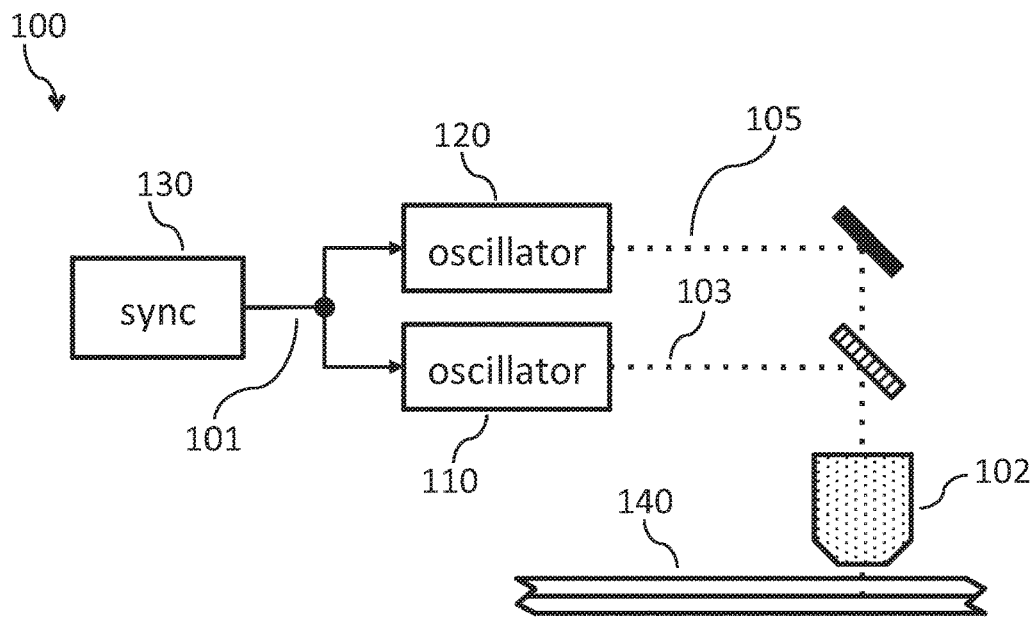
FIG. 1A illustrates a typical approach to CARS spectroscopy of flowing samples.
Figure 1B:
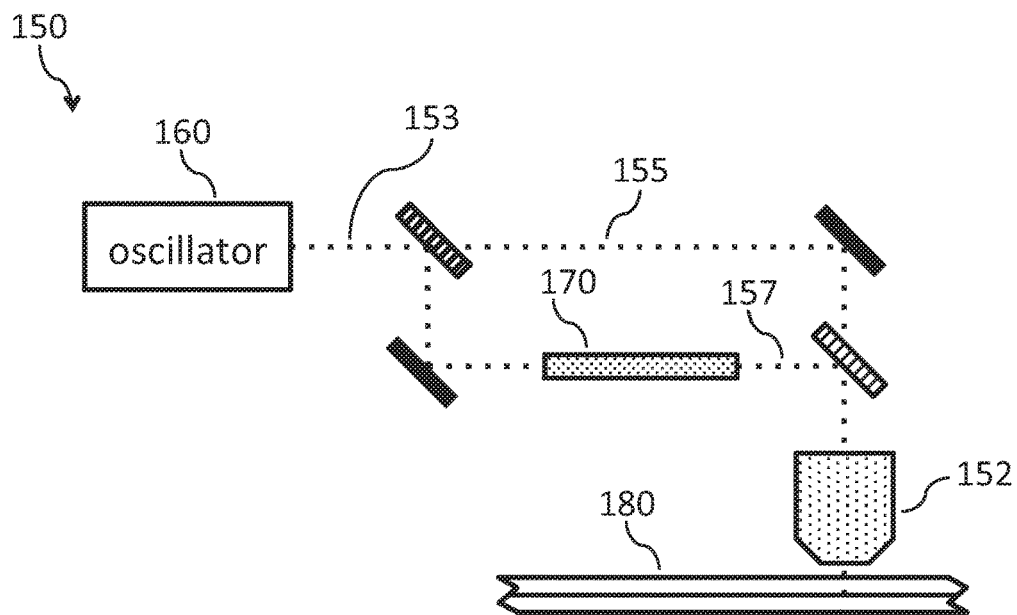
FIG. 1B illustrates a typical approach to CARS spectroscopy of flowing samples.

The embodiments will be described with references to numerous details set forth below, and the accompanying drawings. The following description and drawings are illustrative of the embodiments and are not to be construed as limiting. Numerous specific details are described to provide a thorough understanding of the embodiments as described herein. However, in certain instances, well known or conventional details are not described in order to not unnecessarily obscure the embodiments in detail.

Reference throughout the specification to "at least some embodiments", "another embodiment", or "an embodiment" means that a particular feature, structure, or characteristic described in connection with the embodiment is included in at least some embodiments as described herein. Thus, the appearance of the phrases "in at least some embodiments" or "in an embodiment" in various places throughout the specification are not necessarily all referring to the same embodiment. Furthermore, the particular features, structures, or characteristics may be combined in any suitable manner in one or more embodiments.

In the description herein of the apparatus and its operation, the terms "beam" and "pulse" as referred to the output of pulsed lasers are sometimes used interchangeably. Both terms are accurate and complementary descriptions of pulsed laser outputs; when discussing spatial behavior, the term "beam" more fittingly captures the path that a laser output takes; while, when discussing temporal behavior, the term "pulse" is more appropriate. The term "pulse" will be understood to mean that a light source is on (to illuminate a target) for a period of time and is off (and hence not illuminating the target) for another period of time. In an embodiment, a duration of the pulse is a period of time during which the beam is turned on (to illuminate a target).

Herein, the term "pulse beam" is sometimes used for the avoidance of confusion. It will be appreciated by someone skilled in the art that these various terms reflect different attributes of a single unified entity. Similarly, the terms "wavelength" (represented by "$\lambda$"), "wavenumber" (represented by "$\omega$") and "frequency" (represented by "$\nu$") of an optical pulse or beam, where $\omega=1/\lambda$ and $\nu=c/\lambda$, c being the speed of light, are used interchangeably to describe defining characteristics of the light in such pulse or beam. It will be further appreciated that depictions of elements in the figures provided are schematic and only indicative of relative sizes and configurations, the relative dimensions of several elements having in places been altered from an embodiment for the pursuit of illustrative clarity; that several elements desirable or even necessary for the proper function of the apparatus, for the effective performance of the method, or for both, are not shown in the figures and in several cases are not explicitly mentioned in this description, but would nevertheless be understood by someone skilled in the art as forming implicit part of the apparatus, or contributing implicitly to the method, or both, of the embodiments of the present invention.

DRAWINGS—REFERENCE NUMERALS

| Element number | Element name |
| --- | --- |
| 100 | apparatus of the prior art |
| 101 | control signal |
| 102 | microscope objective |

-continued

| Element number | Element name |
|---|---|
| 103 | pump pulse train |
| 105 | Stokes pulse train |
| 110 | mode-locked laser oscillator |
| 120 | mode-locked laser oscillator |
| 130 | synchronization control module |
| 140 | flowcell |
| 150 | apparatus of the prior art |
| 152 | microscope objective |
| 153 | pulse train |
| 155 | pump pulse train |
| 157 | Stokes pulse train |
| 160 | mode-locked laser oscillator |
| 170 | photonic crystal fiber |
| 180 | flowcell |
| 200 | particle analysis apparatus |
| 201 | pulse beam |
| 202 | beamsplitter |
| 203 | pulse beam |
| 204 | mirror |
| 205 | pulse beam |
| 206 | dispersion control module |
| 207 | pulse beam |
| 208 | variable delay line |
| 209 | Stokes pulse beam |
| 210 | ultrafast amplifier module |
| 211 | Stokes pulse beam |
| 212 | mirror |
| 213 | Stokes pulse beam |
| 214 | dispersion control module |
| 215 | pulse beam |
| 216 | dichroic mirror |
| 217 | pump pulse beam |
| 218 | beam shaper |
| 219 | combined pump-Stokes pulse beam |
| 220 | OPA |
| 221 | combined pump-Stokes pulse beam |
| 222 | dichroic mirror |
| 223 | combined pump-Stokes pulse beam |
| 224 | beam shaper |
| 225 | cw beam |
| 226 | microscope objective |
| 227 | cw beam |
| 228 | flow channel |
| 228' | flow channel |
| 228" | flow channel |
| 229 | cw beam |
| 230 | cw source |
| 231 | cw beam |
| 231' | cw beam |
| 231" | focused cw beam spot |
| 232 | microscope objective |
| 233 | combined pump-Stokes pulse beam |
| 233' | combined pump-Stokes pulse beam |
| 233" | focused combined pump-Stokes beam spot |
| 233'" | combined pump-Stokes pulse train |
| 234 | dichroic mirror |
| 235 | trigger beam |
| 235' | trigger beam |
| 236 | spectral filter |
| 237 | combined CARS pulse beam |
| 237' | combined CARS pulse beam |
| 237" | combined CARS pulse train |
| 238 | photodetector |
| 239 | trigger beam |
| 240 | flowcell |
| 240' | flowcell |
| 240" | flowcell |
| 241 | trigger beam |
| 242 | dichroic mirror |
| 243 | trigger beam |
| 244 | spectral filter |
| 245 | electrical trigger signal |
| 246 | spectral filter |
| 247 | synchronization trigger signal |
| 248 | neutral density filter |
| 249 | electronic time stamp signal |
| 250 | spectrometer |
| 251 | combined CARS pulse beam |
| 252 | photodetector |
| 253 | combined CARS pulse beam |
| 255 | anti-Stokes signal pulse beam |
| 257 | anti-Stokes signal pulse beam |
| 259 | electrical gating signal |
| 260 | photodetector array |
| 261 | coded anti-Stokes spectral signal |
| 263 | altered combined pump-Stokes pulse beam |
| 265 | altered pump pulse beam |
| 267 | altered pump pulse electrical signal |
| 269 | digital packets |
| 270 | synchronization control module |
| 280 | data acquisition module |
| 290 | computer module |
| 300 | frequency-time graph |
| 301 | Stokes center frequency |
| 302 | ellipse |
| 303 | Stokes bandwidth |
| 305 | pump center frequency |
| 306 | ellipse |
| 307 | pump bandwidth |
| 309 | starting pulse duration |
| 310 | time axis |
| 320 | frequency axis |
| 350 | frequency-time graph |
| 352 | Stokes ellipse |
| 353 | Stokes shift |
| 356 | pump ellipse |
| 357 | anti-Stokes shift |
| 359 | stretched pulse duration |
| 363 | anti-Stokes center frequency |
| 364 | anti-Stokes ellipse |
| 365 | anti-Stokes bandwidth |
| 402 | cw wavelength |
| 403 | wavelength |
| 404 | anti-Stokes band |
| 405 | wavelength |
| 406 | pump band |
| 407 | wavelength |
| 408 | Stokes band |
| 410 | wavelength axis |
| 412 | mark |
| 413 | spectral plot |
| 414 | mark |
| 415 | spectral plot |
| 416 | mark |
| 417 | spectral plot |
| 420 | optical transmission axis |
| 423 | spectral plot |
| 425 | spectral plot |
| 427 | spectral plot |
| 500 | particle interrogation region |
| 500' | particle interrogation region |
| 502 | top flowcell wall |
| 504 | bottom flowcell wall |
| 506 | sheath and carrier fluids |
| 506' | sheath and carrier fluids |
| 508 | vector |
| 510 | particle |
| 512 | first cw beam boundary |
| 514 | second cw beam boundary |
| 516 | first CARS beam boundary |
| 518 | second CARS beam boundary |
| 602 | first flowcell sidewall |
| 604 | second flowcell sidewall |
| 700 | flow chart |
| 702 | method operation |
| 704 | method operation |
| 706 | method operation |
| 708 | method operation |
| 710 | method operation |
| 712 | method operation |
| 714 | method operation |
| 716 | method operation |
| 718 | method operation |
| 720 | method operation |

-continued

| Element number | Element name |
| --- | --- |
| 722 | method operation |
| 800 | frequency-time graph |
| 802 | Stokes ellipse |
| 806 | pump ellipse |
| 814 | anti-Stokes ellipse |
| 900 | frequency-time graph |
| 902 | Stokes ellipse |
| 903 | Stokes bandwidth |
| 914 | anti-Stokes ellipse |
| 915 | anti-Stokes bandwidth |
| 1000 | interrogation region |
| 1006 | fluid |
| 1100 | data processing system |
| 1101 | processing unit |
| 1103 | memory |
| 1104 | instructions and data |
| 1105 | display controller |
| 1107 | display device |
| 1109 | non-volatile storage |
| 1111 | I/O controller |
| 1113 | audio input device |
| 1115 | audio output |
| 1117 | I/O device |
| 1119 | digital image input device |
| 1121 | modem or network interface |
| 1123 | bus |

Figure 2:
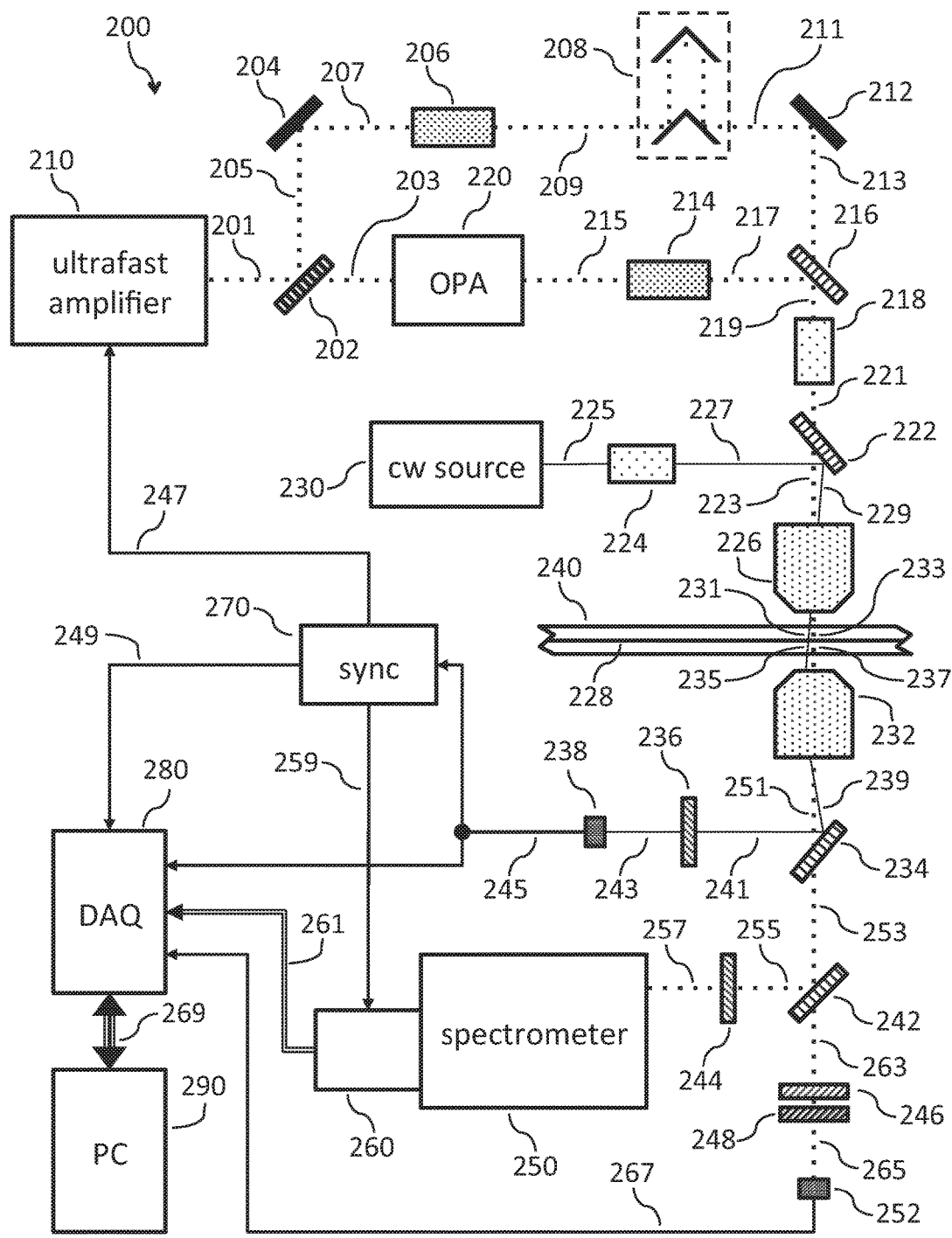
FIG. 2 is a schematic diagram illustrating an apparatus for particle analysis in accordance with one embodiment.

An embodiment of the particle analysis apparatus is illustrated in FIG. 2 (schematic diagram). Particle analysis apparatus 200 comprises an ultrafast pulsed laser amplifier module ("ultrafast amplifier") 210, an ultrafast optical parametric amplifier module ("OPA") 220, a continuous-wave light source ("cw source") 230, a flowcell 240 (partially shown here), a spectrometer 250, a photodetector array 260, a synchronization control module ("sync") 270, a data acquisition module ("DAQ") 280, and a computer module ("PC") 290. Ultrafast amplifier 210 generates a pulse beam 201 that travels to a beamsplitter 202 and is separated into a pulse beam 203 and a pulse beam 205. Pulse beam 205 is redirected by a mirror 204 into a pulse beam 207, which propagates through a dispersion control module 206 and emerges as a Stokes pulse beam 209. Stokes pulse beam 209 travels through a variable delay line 208 and continues as a Stokes pulse beam 211 to a mirror 212, where it reflects into a Stokes pulse beam 213. Stokes pulse beam 213 transmits through a dichroic mirror 216 as a combined pump-Stokes pulse beam 219.

Pulse beam 203 enters OPA 220, which generates a pulse beam 215. Pulse beam 215 propagates through a dispersion control module 214 and emerges as a pump pulse beam 217, which is then reflected by dichroic mirror 216 to combine and overlap with transmitted Stokes pulse beam 213 into combined pump-Stokes pulse beam 219. In at least one embodiment, pump pulse beam 217 and Stokes pulse beam 213 are cross-chirped, as described in further detail below. Combined pump-Stokes pulse beam 219 propagates through a beam shaper 218 and continues as a combined pump-Stokes pulse beam 221 to a dichroic mirror 222, where it is transmitted as a combined pump-Stokes pulse beam 223.

Cw source 230 generates a cw beam 225, which propagates through a beam shaper 224 and continues as a cw beam 227 to dichroic mirror 222, where it is reflected as a cw beam 229. Both cw beam 229 and combined pump-Stokes pulse beam 223 travel through a microscope objective 226 to emerge, respectively, as cw beam 231 and combined pump-Stokes pulse beam 233, and continue to propagate to flowcell 240. Flowcell 240 comprises a flow channel 228 (partially shown here) through which particles to be analyzed move in fluid suspension. In other embodiments such as, e.g., those in which a flow cytometer is not used, a sample holder (such as a microscope slide or other container) holds a fixed, stationary sample. Cw beam 231 and combined pump-Stokes pulse beam 233 are focused by microscope objective 226 in flow channel 228. A more detailed description of the configuration of flow channel 228, of the focused spots of beams 231 and 233, and of their interactions with flowing particles is provided below in reference to FIGS. 5 and 6.

Additionally provided in apparatus 200, but not shown in FIG. 2 in the interest of clarity, are: an extension of partially shown flowcell 240 and partially shown flow channel 228, upstream of the shown portion, that include a hydrodynamic focusing portion for generation of a particle-carrying carrier fluid forming a core sample stream within a sheath fluid; a nozzle for introduction of the particle-carrying carrier fluid; a larger channel for introduction of the sheath fluid; an extension of partially shown flowcell 240 and partially shown flow channel 228, downstream of the shown portion, that include connections and tubing for delivery of interrogated particles, carrier fluid, and sheath fluid to waste; and means of regulating the injection of both the particle-carrying carrier fluid and the sheath fluid, at desired respective rates of volumetric flow, into said nozzle and larger channel and, through said hydrodynamic focusing portion, into the shown portion of flowcell 240 and flow channel 228. Design and incorporation of such elements into apparatus 200 is well known in the art of flow cytometry.

The interaction of cw beam 231, as focused by microscope objective 226 in flow channel 228, with flowing particles under analysis results in a trigger beam 235 that propagates out of flowcell 240, is collected by a microscope objective 232, and emerges as a trigger beam 239, which reflects off of a dichroic mirror 234 as a trigger beam 241, which travels through a spectral filter 236 and propagates as a trigger beam 243 to a photodetector 238. Photodetector 238 converts the optical signal from trigger beam 243 into an electrical trigger signal 245, which is directed to data acquisition module 280, where it is recorded, and to synchronization control module 270. Synchronization control module 270 generates a synchronization trigger signal 247 that is directed to the synchronization and trigger circuitry of ultrafast amplifier module 210, and an electronic time-stamp signal 249 that is directed to data acquisition module 280, where it is recorded.

The interaction of combined pump-Stokes pulse beam 233, as focused by microscope objective 226 into flow channel 228, with flowing particles under analysis results in a combined CARS pulse beam 237 that propagates out of flowcell 240, is collected by microscope objective 232, and emerges as a combined CARS pulse beam 251, which transmits through dichroic mirror 234 as a combined CARS pulse beam 253. Combined CARS pulse beam 253 hits a dichroic mirror 242, where it is separated into an anti-Stokes signal pulse beam 255 and an altered combined pump-Stokes pulse beam 263. Anti-Stokes signal pulse beam 255 is directed through a spectral filter 244 and emerges as an anti-Stokes signal pulse beam 257, which enters spectrometer 250. Spectrometer 250 spectrally disperses anti-Stokes signal pulse beam 257 for detection by a photodetector array 260. Synchronization control module 270 generates an electrical gating signal 259 in response to electrical trigger signal 245, which electrical gating signal 259 is received by photodetector array 260. In response to electrical gating signal 259, photodetector array 260 converts the spectrally dispersed information from anti-Stokes signal pulse beam 257 into a coded anti-Stokes spectral signal 261 that is transmitted to data acquisition module 280, where it is recorded.

Altered combined pump-Stokes pulse beam 263 travels through a spectral filter 246 that rejects its Stokes portion and transmits its pump portion; the transmitted pump portion traverses a neutral-density filter 248 and emerges as an altered pump pulse beam 265, which is received by a photodetector 252 and converted into an altered pump pulse electrical signal 267, which is then transmitted to data acquisition module 280, where it is recorded. Data acquisition module 280 exchanges digital packets 269 (that include control signals, spectral data, and other information) along an electronic communication bus with computer module 290, where further signal processing occurs and where processed data is stored and displayed for the user to inspect, duplicate, or transfer to another system for long-term storage. Computer module 290 further provides an interface with which the user directs the apparatus to perform the particle analysis described herein.

Several elements of the apparatus of an embodiment of the present invention are not shown in FIG. 2 in the pursuit of clarity. For example, among the items not shown are: certain lenses for relay of optical beams; slits and pinholes for spatial filtering of optical beams; probes, syringes, syringe drives, pumps, valves, reservoirs, and tubing for the aspiration, staging, transference, storage, and delivery of particle-containing samples to flowcell 240 for analysis and for disposal of analyzed samples to waste; certain electrical cables for the transmittance of power, control signals, and data signals; mechanical supports; housings; user interfaces for the control and interaction with the apparatus. It will be apparent to someone skilled in the art how these common elements integrate into the apparatus according to an embodiment of the present invention.

Operation

The method and apparatus of an embodiment of the present invention interrogates flowing particles on a single-shot basis (in one embodiment), gathering a broad CARS spectrum from each interaction. By enabling the analysis of an individual particle to occur in the span of a single interrogation event by use of amplified ultrafast optical pulses, an embodiment of the present invention overcomes the shortcomings of the prior art and allows the label-free analysis of particles in flowing samples at high throughput, providing detailed composition information on a particle-by-particle basis without the use of expensive reagents.

Time-Bandwidth Characteristics

Ultrafast amplifier module 210 is a pulsed laser module producing amplified ultrafast pulses of light, typically comprising an ultrafast pulsed laser oscillator, a pump laser for the oscillator, a multipass amplifier, a pump laser for the amplifier, and supporting elements such as, e.g., electrical power supplies, air cooling subsystems, and control and synchronization electronics. A suitable multi-pass amplifier, for example, is a laser amplifier known to those skilled in the art as a regenerative amplifier, based, e.g., on Chirped Pulse Amplification.

The components listed above of ultrafast amplifier module 210 may be separate or they may be integrated into a single subsystem. Internally to ultrafast amplifier module 210, the laser oscillator produces a continuous train of ultrafast optical pulses at repetition rates of about tens of megahertz, each pulse typically being femtoseconds to picoseconds wide and having an energy in an approximate range of a few to a few tens of microjoules. Synchronization trigger signal 247 commands the synchronization and trigger circuitry of ultrafast amplifier module 210 to select individual pulses from the oscillator pulse train, at rates in the Hz to MHz range, with which to seed the multipass amplifier; the multipass amplifier amplifies the energy in such pulse by a factor of up to about a million, and the resulting amplified pulse is delivered from ultrafast amplifier module 210 as pulse beam 201.

OPA 220 is a nonlinear optical module capable of producing ultrafast optical pulses at a wavelength tunable across a wide range of values, starting from an input ultrafast optical pulse at a given wavelength. A typical OPA accepts near-infrared (NIR) pulses around 50 fs long with an energy per pulse on the millijoule scale, and delivers output pulses synchronized with the input pulses, having center wavelengths tunable from the ultraviolet (UV) to the mid-infrared (MIR), and having pulse energies dependent on the tuning wavelength. The wavelength tuning of OPA 220 is adjustable in the method according to an embodiment of the present invention. OPA 220 receives an individual pulse in pulse beam 203 at a center wavelength determined by the narrow tuning parameters of ultrafast amplifier module 210, and it outputs an individual pulse in pulse beam 215 at a center wavelength determined by the broad tuning parameters of OPA 220, such output and input pulses being mutually synchronized.

Figure 3A:
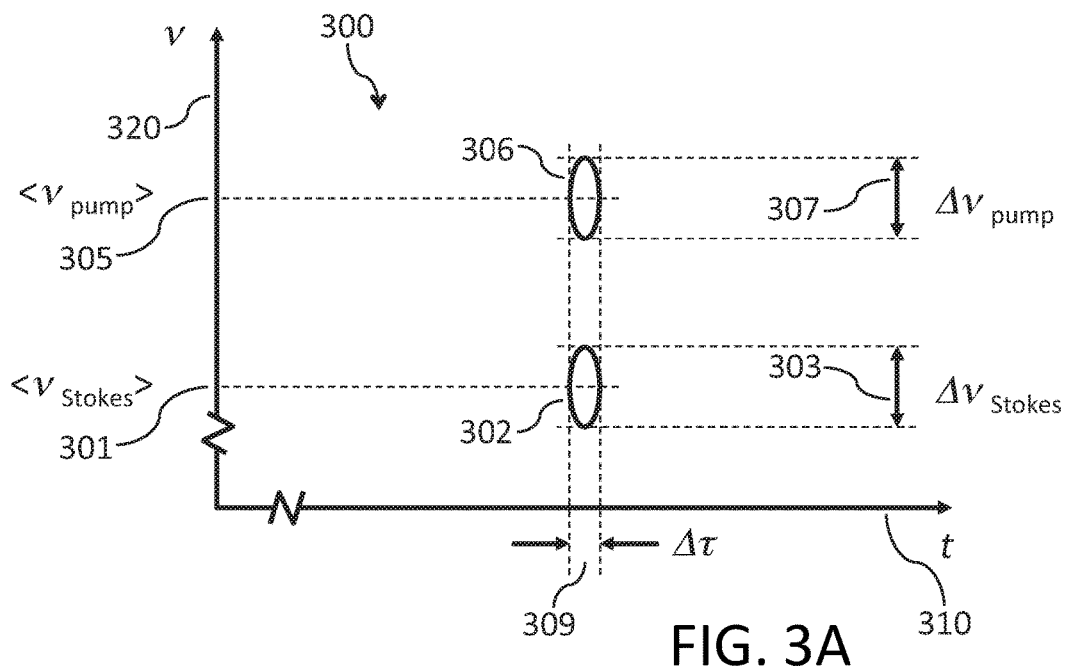
FIG. 3A illustrates a spectroscopic method to be performed on the particle analysis apparatus of FIG. 2 in accordance with one embodiment.
Figure 3B:
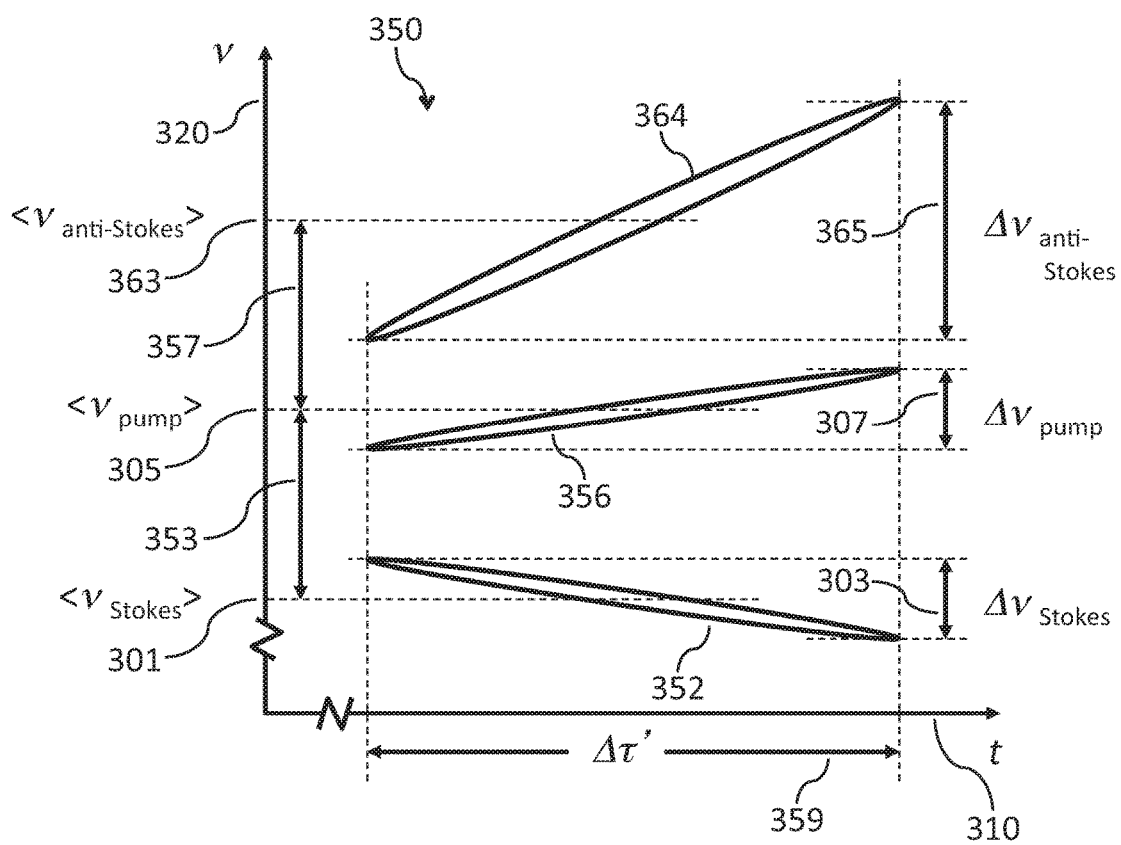
FIG. 3B illustrates a spectroscopic method to be performed on the particle analysis apparatus of FIG. 2 in accordance with one embodiment.

FIGS. 3A and 3B are graphs that illustrate schematically the spectroscopic method according to an embodiment of the present invention. Referring to FIG. 3A and FIG. 2, a time ("t") axis 310 and a frequency ("v") axis 320 are shown, defining a frequency-time graph 300 advantageous to clarify the relationships of various pulse beams of apparatus 200. In optics a relationship can be defined between the duration ("$\Delta\tau$") and the bandwidth ("$\Delta v$") of any given pulse: the product $\Delta\tau \Delta v$, commonly referred to as the time-bandwidth product, under ordinary circumstances has a lower bound. A physical pulse that satisfies this lower bound condition is commonly called "transform-limited," as its temporal and frequency profiles are Fourier transforms of one another. When both the time profile and the frequency profile of such pulse are described by, e.g., Gaussian curves, the lower bound of the time-bandwidth product of a transform-limited pulse assumes the value of 0.44 (with time measured in seconds and frequency in Hertz). A continuous range of values of both duration and bandwidth of any given pulse exists that satisfies the lower-bound limit for the time-bandwidth product. Physical pulses can experience either temporal broadening or frequency broadening or both, resulting in time-bandwidth products larger than the lower bound applicable for the pulse profile in question. In the description herein of the spectroscopic method according to an embodiment of the present invention, and particularly in reference to the frequency-time plots provided in FIGS. 3A and 3B herein, graphical elements such as ellipses are used as mathematical representations of the frequency and temporal characteristics of physical entities such as pulses or pulse beams. Accordingly, the terms "pulse," "beam," "pulse beam," and "ellipse" as referred to the output of pulsed lasers are sometimes used interchangeably. It will be appreciated by someone skilled in the art that these various terms reflect different attributes of a single unified entity. Additionally, in describing characteristics associated with physical or mathematical quantities having a Gaussian, or approximately Gaussian, profile (such as, e.g., the time, frequency, or spatial variation of an ultrafast optical pulse), it is often advantageous for the pursuit of clarity to adopt a convention to symbolically represent the profile in question by two points on either side of the maximum having equal intensity: for example, the two points at the 50% level of intensity that are also used to define the Full Width at Half Maximum (FWHM), or the two points at the 1/e² level of intensity. In FIGS. 3A and 3B, 5A to 5C, and 6, pulses are represented in such a way, with the time and frequency representations in FIGS. 3A and 3B using the FWHM convention and the spatial representations in FIGS. 5A to 5C and 6 using the 1/e² convention.

Referring to FIGS. 2 and 3A, under optimized operation of each of ultrafast amplifier module 210 and OPA 220, the time-bandwidth product for each of pulse beams 201 and 215 can approach or achieve the transform-limited lower bound. An ellipse 302 represents the frequency-time characteristics of ultrafast amplifier module pulse beam 201; the same ellipse, save for horizontal time offsets, represents as well as the frequency-time characteristics of pulse beams 203, 205, and 207, which are substantially unaffected in frequency characteristics by the elements that separate them. An ellipse 306 represents the frequency-time characteristics of OPA pulse beam 215. The relative time offset of pulse beam 215 with respect to pulse beam 201 due to internal propagation in OPA 220 is not shown in FIG. 3A in the interest of clarity. A starting pulse duration ("$\Delta\tau$") 309 is shown to be approximately the same for both ellipse 302 and ellipse 306; a Stokes bandwidth ("$\Delta v_{Stokes}$") 303 of ellipse 302 and a pump bandwidth ("$\Delta v_{pump}$") 307 of ellipse 306 are shown to also have approximately equal value. Ellipse 302 is shown to have a Stokes center frequency ("$<v_{Stokes}>$") 301, and ellipse 306 is shown to have a pump center frequency ("$<v_{pump}>$") 305. Stokes center frequency 301 is shown to be lower than pump center frequency 305 in accordance with pulse beam 201 (as modified by subsequent elements) to act as the CARS pump beam and pulse beam 215 (as modified by subsequent elements) to act as the CARS Stokes beam in the method according to an embodiment of the present invention.

Referring to FIG. 3B, a time ("t") axis 310 and a frequency ("v") axis 320 are shown, defining a frequency-time graph 350 analogous to that defined by axes 310 and 320 in FIG. 3A. Referring to FIGS. 3A, 3B, and 2, propagation of pulse beams 207 and 215 through, respectively, dispersion control modules 206 and 214 in apparatus 200 according to an embodiment of the present invention causes changes in their respective frequency-time characteristics. Dispersion generally signifies the different behavior experienced by beams, or portions of beams, having different optical frequencies (or, equivalently, wavelengths). In this context, dispersion indicates the different propagation delays experienced by different frequency components of a pulse beam as such pulse beam propagates through a given material. Accordingly, pulse beam 215 (represented by ellipse 306) transits through dispersion control module 214, which is chosen so as to impart positive dispersion to a pulse beam transiting through it; the resulting pump pulse beam 217 is represented in FIG. 3B as a pump ellipse 356. A pulse of the kind represented by pump ellipse 356 is said to have positive "chirp," where chirp, in analogy to acoustics, indicates the progressive change in frequency content of an extended pulse as the pulse evolves in time: positive chirp indicates a progressive increase in frequency content of a pulse over its duration. This temporal evolution can be traced in FIG. 3B by going from left to right along pump ellipse 356: the frequency of each portion of the pulse that the ellipse represents shifts higher and higher from the beginning (left) to the end (right) of the pulse (ellipse).

Pulse beam 201 (represented by ellipse 302) first undergoes two reflections that do not significantly influence its frequency characteristics, and then transits through dispersion control module 206, which is chosen so as to impart negative dispersion to a pulse beam transiting through it; the resulting Stokes pulse beam 209 is represented in FIG. 3B as a Stokes ellipse 352. A pulse of the kind represented by Stokes ellipse 352 is said to have negative chirp: the frequency of each portion of the pulse that the ellipse represents shifts lower and lower from the beginning (left) to the end (right) of the pulse (ellipse).

Propagation through dispersive control modules 206 and 214 produces an increase in the temporal spread ("stretch") of each of pulse beams 209 and 217 with respect to the temporal spread of each of pulse beams 207 and 215, respectively. Referring to FIGS. 3A and 3B, this increase is represented by a stretched pulse duration ("$\Delta\tau'$") 359, which is shown to be approximately the same for both Stokes pulse beam 209 (represented by Stokes ellipse 352) and pump pulse beam 217 (represented by pump ellipse 356), and also considerably larger than starting pulse duration 309.

Neither the bandwidths nor the center frequencies of either pulse beam 215 or pulse beam 207 are significantly affected by propagation through dispersive elements. Accordingly, a Stokes center frequency $<v_{Stokes}>$ 301 of Stokes ellipse 352 (Stokes pulse beam 209) in FIG. 3B is shown to be approximately the same as Stokes center frequency $<v_{Stokes}>$ 301 of ellipse 302 (pulse beam 207) in FIG. 3A, and a pump center frequency $<v_{pump}>$ 305 of pump ellipse 356 (pump pulse beam 217) in FIG. 3B is shown to be approximately the same as pump center frequency $<v_{pump}>$ 305 of ellipse 306 (pulse beam 215) in FIG. 3A. Similarly, a Stokes bandwidth $\Delta v_{Stokes}$ 303 of Stokes ellipse 352 in FIG. 3B is shown to be approximately the same as Stokes bandwidth $\Delta v_{Stokes}$ 303 of ellipse 302 in FIG. 3A, and a pump bandwidth $\Delta v_{pump}$ 307 of pump ellipse 356 in FIG. 3B is shown to be approximately the same as pump bandwidth $\Delta v_{pump}$ 307 of ellipse 306 in FIG. 3A.

The relative time offset of Stokes pulse beam 209 as it emerges past variable delay line 208 as Stokes pulse beam 211 is not shown in the interest of clarity. Likewise, the effect of subsequent propagation of Stokes pulse beam 213 and pump pulse beam 217 through possibly dispersive material, such as beam shaper 218, dichroic mirror 222, microscope objective 226, flowcell 240, and the sheath and carrier fluids in flow channel 228, is not shown in the interest of clarity. The setting of variable delay line 208 is adjusted during calibration of apparatus 200 in order to cause optimal temporal overlap of the pump and Stokes pulses in combined pump-Stokes pulse beam 233 at the point of interrogation in flow channel 228. This optimal temporal overlap is schematically represented in FIG. 3B by the vertical alignment of ellipses 352 and 356. Likewise, the overall dispersion of the pump and Stokes beams through all the optical elements the two beams traverse in their path to the sample is accounted for in the design and operation of dispersion control modules 206 and 214, which are adjusted and set to result in the desired frequency characteristics of each beam [as schematically represented in FIG. 3B] at the point of interrogation.

Referring to FIGS. 2 and 3B, the coherent interaction of the positively chirped pump pulse beam 217 (ellipse 356) and the negatively chirped Stokes pulse beam 213 (ellipse 352) with material from particles under analysis in flow channel 228 results in the generation of the anti-Stokes portion of combined CARS pulse beam 237. Chirping, and the attendant temporal stretching, of the pump and Stokes pulse beams tends to minimize non-resonant background and other nonlinear factors (such as second-harmonic generation) that would act to distort and mask the CARS signal. In this embodiment, the anti-Stokes signal being collected is essentially co-propagating with both the pump pulse beam and the Stokes pulse beam as combined CARS pulse beam 237. The anti-Stokes portion of the pulse beam that carries the desired CARS signal is separated from the rest of the CARS pulse beams as anti-Stokes signal pulse beam 257. An anti-Stokes ellipse 364 represents the frequency-time characteristics of anti-Stokes signal pulse beam 257. The form of anti-Stokes ellipse 364 indicates schematically, in one embodiment, the effect of the CARS process that generates the desired anti-Stokes signal: (i) stretched pulse duration $\Delta\tau$ 359 of anti-Stokes ellipse 364 is shown to be approximately the same as that of both Stokes ellipse 352 and pump ellipse 356; (ii) an anti-Stokes shift 357 between an anti-Stokes center frequency $<v_{anti\text{-}Stokes}>$ 363 of anti-Stokes ellipse 364 and pump center frequency $<v_{pump}>$ 305 is shown to be approximately equal to a Stokes shift 353 between pump center frequency $<v_{pump}>$ 305 and Stokes center frequency $<v_{Stokes}>$ 301; and (iii) an anti-Stokes bandwidth (" $\Delta v_{anti\text{-}Stokes}$ ") 365 of anti-Stokes ellipse 364 is shown to be approximately equal to the sum of Stokes bandwidth $\Delta v_{Stokes}$ 303 and twice pump bandwidth $\Delta v_{pump}$ 307 in accordance with the CARS process.

Dispersion control module 214 is designed to impart positive chirp to pulse beam 215. Positive chirp is the effect of what is commonly referred to as normal dispersion in transparent media in the range of wavelengths from the UV (ultraviolet) to the NIR (near infrared). Such dispersion (characterized by a positive Group Velocity Dispersion, or GVD) causes higher-optical-frequency waves to travel slower through such media, and therefore to emerge out of such media with longer delays, than waves with lower optical frequency. Accordingly, dispersion control module 214 comprises a length of material transparent, and with a known group velocity dispersion, over the wavelength range of pulse beam 215, such length and group velocity dispersion being chosen so as to produce the desired degree of chirp and temporal stretching in pump pulse beam 217.

Dispersion control module 206 is designed to impart negative chirp to pulse beam 207. To achieve negative chirp, dispersion control module 206 comprises dispersive elements arranged so as to cause an overall anomalous dispersion through dispersion control module 206. Such dispersion (characterized by a negative Group Velocity Dispersion, or GVD) causes higher-optical-frequency waves to travel faster through such module, and therefore to emerge out of such media with shorter delays, than waves with lower optical frequency. Devices generally known as pulse compressors, comprising, e.g., sets of matched dispersive prisms arranged to produce negative chirp by angular dispersion, are well known in the art, as are other arrangements of dispersive elements such as, e.g., matched grating pairs. Such devices are generally used in the prior art to impart negative chirp to compensate for unwanted positive chirp and therefore achieve maximally compressed pulses. In the method and apparatus according to an embodiment, devices of such design are used for the opposite purpose, i.e., to stretch short pulses by imparting a negative chirp. Accordingly, dispersion control module 206 comprises a set of matched dispersive elements transparent over the wavelength range of pulse beam 207 arranged to produce, by angular dispersion, the desired degree of negative chirp and temporal stretching in Stokes pulse beam 209.

Spectral Characteristics

Figure 4A:
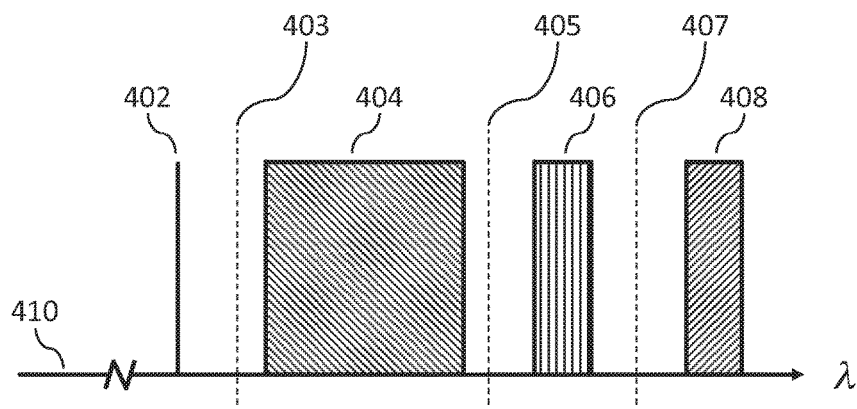
FIG. 4A shows a graph illustrating relationships among spectral characteristics of certain items of FIG. 2 in accordance with one embodiment.
Figure 4B:
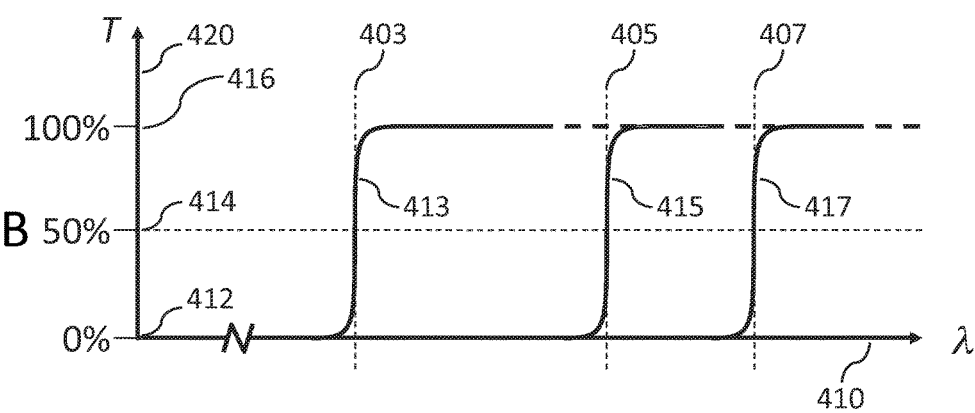
FIG. 4B shows a graph illustrating relationships among spectral characteristics of certain items of FIG. 2 in accordance with one embodiment.
Figure 4C:
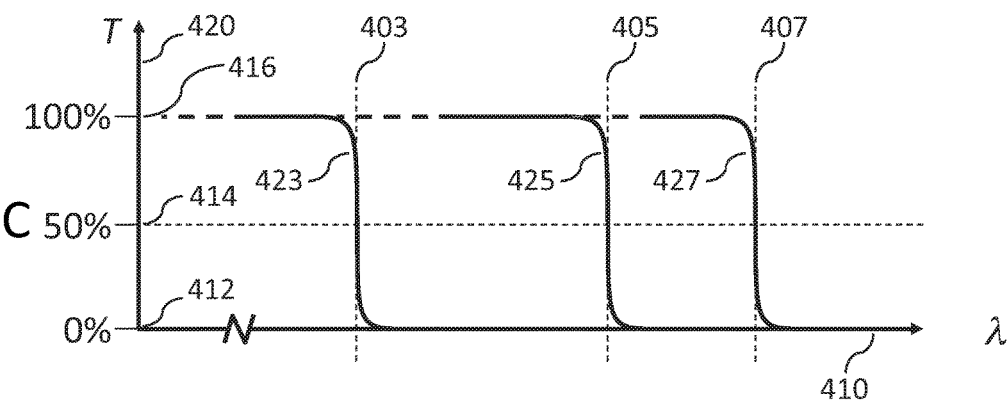
FIG. 4C shows a graph illustrating relationships among spectral characteristics of certain items of FIG. 2 in accordance with one embodiment.

FIGS. 4A to 4C are graphs that illustrate schematically the spectral relationships among several elements of particle analysis apparatus 200 according to an embodiment. Referring to FIG. 4A, several spectral bands are shown along a wavelength ("$\lambda$") axis 410 to indicate their approximate relative values. Starting with lower wavelength values at the left, one encounters first a cw wavelength 402, representing the wavelength of cw source 230; an anti-Stokes band 404, representing the wavelength range of anti-Stokes signal pulse beam 257; a pump band 406, representing the wavelength range of pump pulse beam 217 (and also of pulse beam 215); and a Stokes band 408, representing the wavelength range of Stokes pulse beams 209, 211, and 213 (and also of pulse beams 201, 205, and 207). A wavelength 403 is shown, between cw wavelength 402 and anti-Stokes band 404, chosen so as not to overlap with either cw wavelength 402 or anti-Stokes band 404. Likewise, a wavelength 405 is shown, between anti-Stokes band 404 and pump band 406, chosen so as not to overlap with either anti-Stokes band 404 or pump band 406. Likewise, a wavelength 407 is shown, between pump band 406 and Stokes band 408, chosen so as not to overlap with either pump band 406 or Stokes band 408. Wavelengths 403, 405, and 407 are shown also in FIGS. 4A to 4C to facilitate comparison.

FIG. 4B is a schematic graph of the spectral characteristics of several dichroic elements of particle analysis apparatus 200, plotted on an optical transmission ("T") axis 420 vs. a wavelength ("$\lambda$") axis 410. Axis 410 in FIG. 4B is analogous to axis 410 in FIG. 4A, and the two axes are mutually aligned to illustrate the relationships between the wavelength bands of FIG. 4A and the spectral characteristics of FIG. 4B. Axis 420 bears a mark 412 indicating the value of 0%, representing zero transmission; a mark 414 indicating the value of 50%, representing 50% transmission; and a mark 416 indicating the value of 100%, representing 100% transmission. In optical transmission graphs of the kind illustrated in FIG. 4B, as long as absorption and scattering losses of the plotted elements are negligible, one can also extract values of optical reflection as the complement of optical transmission: therefore, a point showing transmission of 0% also indicates reflection of 100%; one showing transmission of 50% also indicates reflection of 50%; and one showing transmission of 100% also indicates reflection of 0%; and similarly for all points in between 0% and 100%.

Starting from the lower wavelength values at the left, one encounters first a spectral plot 413, representing the optical transmission of both dichroic mirror 222 and dichroic mirror 234; then a spectral plot 415, representing the optical transmission of dichroic mirror 242; and a spectral plot 417, representing the optical transmission of dichroic mirror 216. Each of spectral plots 413, 415, and 417 shows a transition, going from short to long wavelengths, from a behavior of very low transmission and very high reflection to a behavior of very high transmission and very low reflection. This type of spectral behavior is commonly referred to as "longpass" on account of the fact that longer wavelengths are passed through the corresponding element and shorter wavelengths are reflected by it.

The wavelength where each plot crosses the T=50% level is called the edge wavelength ("$\lambda_{edge}$") of the corresponding dichroic mirror: The $\lambda_{edge}$ of the dichroic mirrors represented by plot 413 matches wavelength 403, the $\lambda_{edge}$ of the mirror represented by plot 415 matches wavelength 405, and the $\lambda_{edge}$ of the mirror represented by plot 417 matches wavelength 407. The edge wavelengths of the dichroic mirrors in the apparatus according to an embodiment of the present invention are chosen so as to respond differently to appropriate wavelength bands and act either as beam combiners or as beam splitters, depending on the configuration.

Accordingly, the $\lambda_{edge}$ shown by wavelength 403 is chosen so that the behavior indicated by plot 413 is to reflect cw wavelength 402 and transmit anti-Stokes band 404, pump band 406, and Stokes band 408. Therefore, in the configuration shown in FIG. 2, dichroic mirror 222 acts as a beam combiner and dichroic mirror 234 acts as a beam splitter for the sets of wavelengths indicated. Similarly, the $\lambda_{edge}$ shown by wavelength 405 is chosen so that the behavior indicated by plot 415 is to reflect anti-Stokes band 404 and transmit pump band 406 and Stokes band 408. Dichroic mirror 242 acts therefore as a beam splitter, in the configuration shown in FIG. 2, for the sets of wavelengths indicated. And the $\lambda_{edge}$ shown by wavelength 407 is chosen so that the behavior indicated by plot 415 is to reflect pump band 406 and transmit Stokes band 408. Dichroic mirror 216 acts therefore as a beam combiner, in the configuration shown in FIG. 2, for the sets of wavelengths indicated.

FIG. 4C is a schematic graph of the spectral characteristics of several filter elements of particle analysis apparatus 200, plotted on optical transmission ("T") axis 420 vs. a wavelength ("λ") axis 410. Axis 410 in FIG. 4C is analogous to axis 410 in FIG. 4A and axis 410 in FIG. 4B, and the three axes are mutually aligned to illustrate the relationships between the wavelength bands of FIG. 4A and the spectral characteristics of FIGS. 4B and 4C. Axis 420 bears a mark 412 indicating the value of 0%, representing zero transmission; a mark 414 indicating the value of 50%, representing 50% transmission; and a mark 416 indicating the value of 100%, representing 100% transmission. Representation of optical transmission and optical reflection in the graph of FIG. 4C is analogous to that in the graph of FIG. 4B. Starting from the lower wavelength values at the left, one encounters first a spectral plot 423, representing the optical transmission of filter 236; then a spectral plot 425, representing the optical transmission of filter 244; and a spectral plot 427, representing the optical transmission of filter 246. Each of these plots shows a transition, going from short to long wavelengths, from a behavior of very high transmission and very low reflection to a behavior of very low transmission and of very high reflection. This type of spectral behavior is commonly referred to as "shortpass" on account of the fact that shorter wavelengths are passed through the corresponding element and longer wavelengths are reflected by it.

The wavelength where each plot crosses the T=50% level is called the edge wavelength $\lambda_{edge}$ of the corresponding filter: The $\lambda_{edge}$ of the filter represented by plot 423 matches wavelength 403, the $\lambda_{edge}$ of the filter represented by plot 425 matches wavelength 405, and the $\lambda_{edge}$ of the filter represented by plot 427 matches wavelength 407. The edge wavelengths of the filters in the apparatus according to an embodiment of the present invention are chosen so as to increase the degree of rejection of undesired wavelength bands.

Accordingly, the $\lambda_{edge}$ shown by wavelength 403 is chosen so that the behavior of filter 236 indicated by plot 423 is to transmit and accept cw wavelength 402 and reflect and reject anti-Stokes band 404, pump band 406, and Stokes band 408. Similarly, the $\lambda_{edge}$ shown by wavelength 405 is chosen so that the behavior of filter 244 indicated by plot 425 is to transmit and accept anti-Stokes band 404 and reflect and reject pump band 406 and Stokes band 408. And the $\lambda_{edge}$ shown by wavelength 407 is chosen so that the behavior of filter 246 shown by plot 427 is to transmit and accept pump band 406 and reflect and reject Stokes band 408.

Cw source 230 is designed to produce a beam to be used as a trigger for ultrafast amplifier module 210 and OPA 220 of particle analysis apparatus 200. Referring to FIGS. 2 and 4A, cw wavelength 402 is designed to be shorter than the shortest wavelength in anti-Stokes band 404. This design requirement translates in practice in ensuring a sufficient spectral gap between cw wavelength 402 and anti-Stokes band 404 so that a reasonably manufacturable long-pass dichroic mirror 234 will transmit a majority of anti-Stokes band 404 of the light in combined CARS pulse beam 251 while reflecting a majority of cw wavelength 402 in trigger beam 239. The spectral cutoff profiles of commercially available longpass dichroic filters and the range of wavelengths of commercially available cw sources are sufficient to ensure that this is the case.

Photodetector 238 is chosen to have an appropriately sensitive response at cw wavelength 402, and a sufficiently fast response to produce an electrical signal that closely approximates the actual temporal variation of optical signal 243 incident upon it. Integrated into photodetector 238, or adjunct to it, is signal-amplifying circuitry that boosts the level of electrical trigger signal 245 in a predominantly linear proportional relationship to the level of optical signal 243 received by photodetector 238.

Beamsplitter 202 is designed to have an essentially flat spectral response across Stokes band 408 of pulse beam 201. It is further designed to transmit a majority of the light incident upon it as pulse beam 203, and reflect the balance as pulse beam 205. The energy per pulse of OPA output pulse beam 215 depends on the specific wavelength OPA 220 is tuned to. Accordingly, as the intent is generally for combined pump-Stokes pulse beam 233 to deliver approximately comparable pulse energies in the Stokes pulse and in the pump pulse to the particles under analysis, the transmission/reflection ratio for beamsplitter 202 is chosen in support of that goal, taking in consideration the efficiency of light conversion taking place in OPA 220 at the chosen tuning wavelength.

Mirrors 204 and 212 are designed to have an essentially flat spectral response across Stokes band 408 of pulse beam 203 and Stokes pulse beam 211. The internal mirrors that comprise variable delay line 208 are likewise designed to have a similarly flat response across Stokes band 408.

Neutral-density filter 248 is designed to have an essentially flat spectral response across pump band 406 and, therefore, of the portion of altered combined pump-Stokes pulse beam 263 that is transmitted through filter 246. Neutral-density filter 248 is further designed to have a sufficient optical density, or opacity, to reduce the peak power of altered pump pulse beam 265 to levels below both the optical damage threshold and the limit of linear response of photodetector 252.

Photodetector 252 is chosen to have an appropriately sensitive spectral response to pump band 406, and a time response as fast as practical to produce an electrical signal that introduces the least distortion into the actual temporal variation of optical signal 265 incident upon it. Integrated into photodetector 252, or adjunct to it, is signal-amplifying circuitry that boosts the level of altered pump pulse electrical signal 267 in a predominantly linear proportional relationship to the level of optical signal 265 received by photodetector 252.

Spectrometer 250 is designed to spectrally disperse the wavelength components of anti-Stokes signal pulse beam 257 in such a way as to permit their detection and resolution by photodetector array 260. Spectrometer 250 may consist of gratings, prisms, or other spectrally dispersive elements, and it may consist of a single stage, a double stage, or more, as appropriate to provide the desired spectral resolution without unduly sacrificing sensitivity.

Photodetector array 260 may be, e.g., a CCD camera, a CMOS camera, a sensor array, a photomultiplier array, or any other suitable device capable of detecting with sufficient sensitivity light levels along a collection of discrete positions disposed in a direction aligned with the direction of spectral dispersion by spectrometer 250. Photodetector array 260 is chosen to have an appropriately sensitive spectral response to anti-Stokes band 404 generated by the interaction of combined pump-Stokes pulse beam 233 with particles under analysis. Photodetector 260 may further be designed to allow for cooling of its active sensor elements in order to reduce background electrical noise. Photodetector array 260 is further designed to allow for activation and deactivation of its sensing function by gating signal 259 on a timescale as comparable as possible to the duration of any single pulse in anti-Stokes signal pulse beam 257.

Geometry and Temporal Characteristics

Figure 5A:
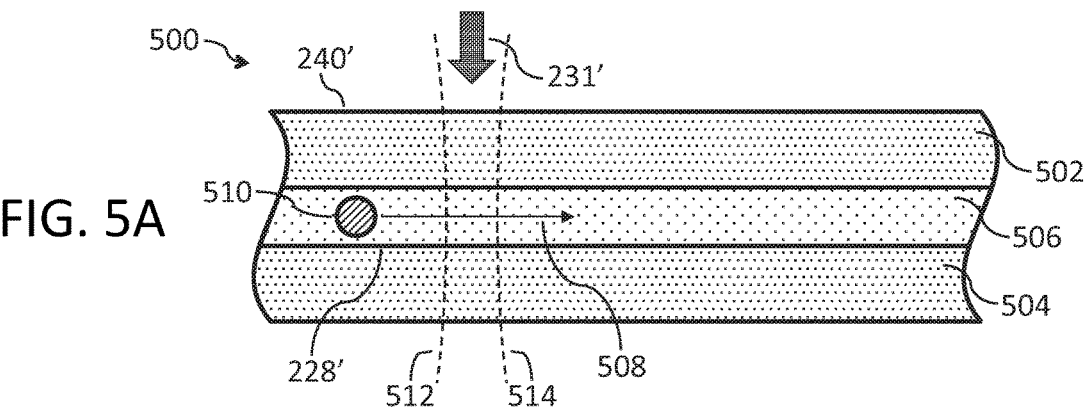
FIG. 5A is a schematic representation of aspects of a sequence of particle interrogation events involving the apparatus of FIG. 2 in accordance with one embodiment.
Figure 5B:
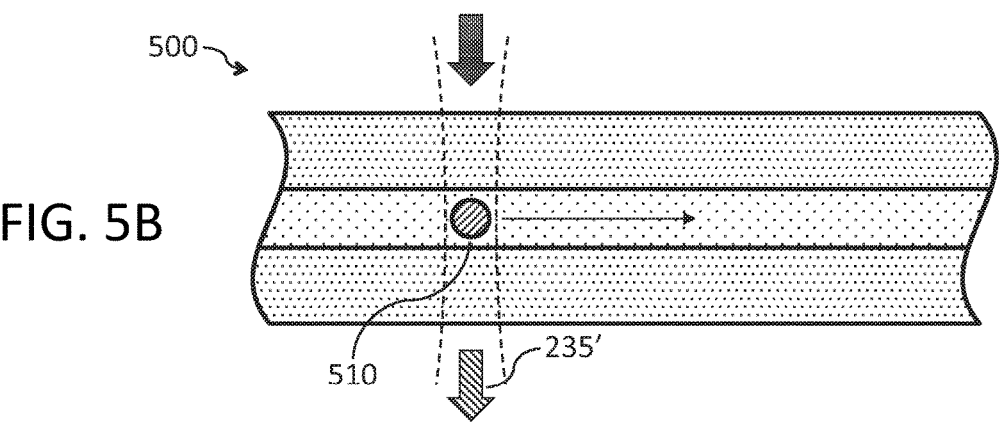
FIG. 5B is a schematic representation of aspects of a sequence of particle interrogation events involving the apparatus of FIG. 2 in accordance with one embodiment.
Figure 5C:
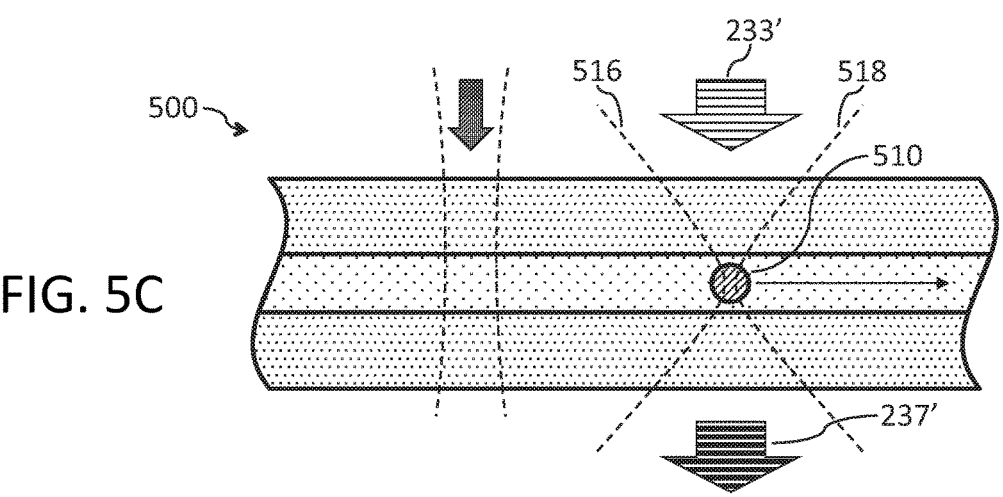
FIG. 5C is a schematic representation of aspects of a sequence of particle interrogation events involving the apparatus of FIG. 2 in accordance with one embodiment.

FIGS. 5A to 5C are side-view cross-sectional schematic representations of the particle interrogation region in the apparatus according to an embodiment of the present invention that illustrate the relative configurations of the interrogating beams in relationship to the flow channel and particles therein, at three instances of time depicting the progression of a particle under analysis within the flow channel. Referring to FIG. 5A, a particle interrogation region 500 is shown comprising portion of flowcell 240 from FIG. 2 shown here as a flowcell 240' and portion of flow channel 228 from FIG. 2 shown here as a flow channel 228' within flowcell 240', both flowcell and flow channel being shown as sectioned along a vertical midplane that contains both the central axis of the flow channel and the central axes of the interrogating beams. Further shown in FIG. 5A are portion of a top flowcell wall 502, portion of a bottom flowcell wall 504, portion of sheath and carrier fluids 506, a vector 508 indicating direction and velocity of fluid flow and of particle motion, portion of cw beam 231 from FIG. 2 shown here as a cw beam 231', a first cw beam boundary 512 of cw beam 231', a second cw beam boundary 514 of cw beam 231', and a particle 510 at a time when its position in flow channel 228' is upstream of cw beam 231'. Referring to FIGS. 5B and 2, particle interrogation region 500 is shown at a later time when particle 510 has advanced to a position of overlap with cw beam 231', the interaction with which transiently generates trigger beam 235, portion of which is shown here as a trigger beam 235'. Referring to FIG. 5C, particle interrogation region 500 is shown, additionally comprising portion of combined pump-Stokes pulse beam 233 from FIG. 2 shown here as a combined pump-Stokes pulse beam 233', a first CARS beam boundary 516 of combined pump-Stokes pulse beam 233', and a second CARS beam boundary 518 of combined pump-Stokes pulse beam 233', at a time later yet when particle 510 has further advanced to a position of overlap with combined pump-Stokes pulse beam 233', the interaction of which transiently generates combined CARS pulse beam 237, portion of which is shown here as a combined CARS pulse beam 237'. Depictions of elements in the cross-sectional views of FIGS. 5A to 5C are schematic and only indicative of relative sizes and configurations, the relative dimensions of several elements being illustrated differently from an embodiment for the pursuit of illustrative clarity. For example, particle 510 is shown as only slightly smaller than the height of flow channel 228', whereas in practice it would be advantageous for particle 510 to be considerably smaller than the height of flow channel 228'. Also in the way of example, the sheath fluid and the particle-carrying carrier fluid forming a core sample stream within the sheath fluid are not separately demarcated in FIGS. 5A to 5C.

In FIGS. 5A to 5C, cw beam 231' and combined pump-Stokes pulse beam 233' are schematically represented by boundaries, respectively 512 and 514, and 516 and 518. These boundaries represent idealizations of the waist of the beam in each case, and specifically the locations in each horizontal plane of the $1/e^2$ levels of intensity in the respective spatial profiles, following common practice in Gaussian optics and the convention outlined above with respect to representations of Gaussian profiles. In practice, the intensity profiles of real beams have generally more gradual transition than the indication of a boundary might suggest. Accordingly, the extent of each beam in practice reaches beyond the boundaries schematically indicated, although generally with decreasing intensity.

Cw beam 231' is shown present at all the times represented in FIGS. 5A to 5C, reflecting the fact that it is a beam from a cw source. On the other hand, combined pump-Stokes pulse beam 233' is shown only present at the time represented in FIG. 5C, reflecting the fact that it is a beam from an ultrafast pulsed source. Pulse beam 233' is only generated in response to the transit of particles through the interrogation region as indicated schematically by the sequence illustrating the process for particle 510 in FIGS. 5A to 5C, and it is specifically triggered by the passing of such particles through the region illuminated by cw beam 231'.

Figure 6:
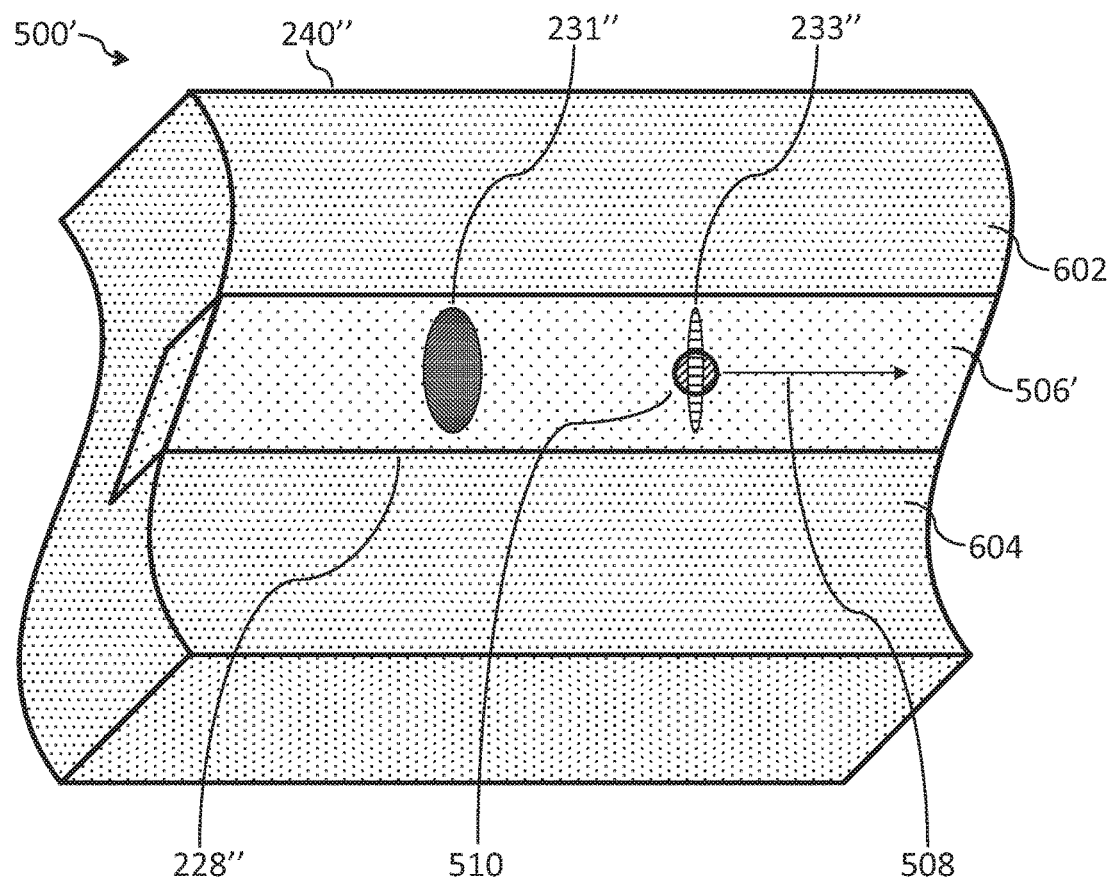
FIG. 6 is a perspective view of the particle interrogation region of the flow channel of FIG. 2 in accordance with one embodiment.

FIG. 6 is a perspective view of a cross-sectional schematic representation of the particle interrogation region of flow channel 228 to illustrate the relative configurations of the interrogating beams in relationship to the flow channel and particles therein. Referring to FIG. 6, a view of particle interrogation region 500 from FIGS. 5A to 5C is shown here as a particle interrogation region 500', comprising a view of flowcell 240' from FIGS. 5A to 5C shown here as a flowcell 240", a view of flow channel 228' from FIGS. 5A to 5C shown here as a flow channel 228" within flowcell 240", both flowcell and flow channel being shown as sectioned along a horizontal midplane that contains the central axis of the flow channel and is approximately perpendicular to the propagation direction of the interrogating beams. Further shown in FIG. 6 are a first flowcell sidewall 602, a second flowcell sidewall 604, sheath and carrier fluids 506', vector 508 indicating direction and velocity of fluid flow and of particle motion, portion of cw beam 231 from FIG. 2 shown here as a focused cw beam spot 231", portion of combined pump-Stokes pulse beam 233 from FIG. 2 shown here as a focused combined pump-Stokes beam spot 233", and particle 510 in a position of overlap with focused combined pump-Stokes beam spot 233" corresponding to the time represented also in FIG. 5C.

Depictions of elements in the cross-sectional view of FIG. 6 are schematic and only indicative of relative sizes and configurations, the presence and position of several elements being illustrated differently from an embodiment for the pursuit of illustrative clarity. For example, focused cw beam spot 231" and focused combined pump-Stokes beam spot 233" are shown as only slightly smaller than the width of flow channel 228", whereas in practice it would be advantageous for both beam spots to be considerably smaller than the width of flow channel 228'. Also in the way of example, the sheath fluid and the particle-carrying carrier fluid forming a core sample stream within the sheath fluid are not separately demarcated in FIG. 6. Further, focused cw beam spot 231" and focused combined pump-Stokes beam spot 233" are schematically represented by ellipses. These ellipses represent idealizations of the waist of the beam in each case, and specifically the locations, in the focal plane of microscope objective 226, of the $1/e^2$ levels of intensity in the respective spatial profiles, following common practice in Gaussian optics and the convention outlined herein with respect to representations of Gaussian profiles. In practice, the intensity profiles of real beams have generally more gradual transition than the indication of a line boundary might suggest. Accordingly, the extent of each beam in practice reaches beyond the ellipses schematically indicated, although generally with decreasing intensity.

Beam shaper 218 shapes combined pump-Stokes pulse beam 219 in such a way as to achieve, in conjunction with microscope objective 226, the desired optical properties for focused combined pump-Stokes beam spot 233" in the focal plane of microscope objective 226 in flow channel 228. Output pulse beams 201 and 215 from, respectively, ultrafast amplifier module 210 and OPA 220 generally are collimated, have approximately Gaussian profiles, and have circular or elliptical cross sections. Beam shaper 218 is designed, by selection and placement of such appropriate refractive or reflective elements as may comprise it (such as, e.g., diverging and converging lenses or mirrors; where both lenses or mirrors may be spherical to affect equally both cross-sectional dimensions of the beam; or both lenses or mirrors may be cylindrical, to affect one cross-sectional dimension of the beam but not the other), to alter combined pump-Stokes pulse beam 219 and produce optical characteristics (including, e.g., dimensions, a cross-sectional aspect ratio, and a divergence) of combined pump-Stokes pulse beam 221 to result, in the focal plane of microscope objective 226 in flow channel 228, in a focused combined pump-Stokes beam spot 233" with desired optical characteristics (such as, e.g., dimensions, a cross-sectional aspect ratio, and a divergence in at least one dimension in a desired range of values in order to satisfy as broadly as possible wavevector sum rules for CARS processes).

Beam shaper 224 shapes cw beam 225 in such a way as to achieve, in conjunction with microscope objective 226, the desired optical properties for focused cw beam spot 231" in the focal plane of microscope objective 226 in flow channel 228. Output cw beam 225 from cw source 230 is generally chosen to be collimated, have an approximately Gaussian profile, and have a circular or elliptical cross section. Beam shaper 224 is designed, by selection and placement of appropriate refractive or reflective elements as may comprise it (such as, e.g., diverging and converging lenses or mirrors; where both lenses or mirrors may be spherical to affect equally both cross-sectional dimensions of the beam; or both lenses or mirrors may be cylindrical, to affect one cross-sectional dimension of the beam but not the other), to alter cw beam 225 and produce optical characteristics (including, e.g., dimensions, a cross-sectional aspect ratio, and a divergence) of cw beam 227 to result, in the focal plane of microscope objective 226 in flow channel 228, in a focused cw beam spot 231" with desired optical characteristics (such as, e.g., dimensions, a cross-sectional aspect ratio, and a divergence in a desired range of values in order to confer to cw beam 231' a sufficient depth of focus).

Microscope objective 226 is designed to focus combined pump-Stokes pulse beam 223 and cw beam 229 onto particles under analysis in the focal plane of microscope objective 226, approximately in the midplane of flow channel 228, and to produce the desired dimensions of focused combined pump-Stokes pulse beam spot 233" and focused cw beam spot 231". The beam focusing geometry is calculated to satisfy with high tolerance the CARS wavevector sum rules in the plane defined by the propagation axis of combined pump-Stokes beam 233' and vector 508. A suitable choice of microscope objective 226 is an air-gap, long-working-distance, infinity-corrected achromatic objective.

Microscope objective 232 is designed to collect the greatest portion of combined CARS pulse beam 237' generated in the course of the interaction between combined pump-Stokes pulse beam 233' and particle 510, and to relay the light thus collected to spectrometer 250 through the intervening optical elements. Microscope objective 232 is secondarily designed to also collect a sufficient portion of trigger beam 235 to allow for the reliable detection of particles flowing in flow channel 228 and subsequent triggering of ultrafast amplifier module 210 and OPA 220. A suitable choice of microscope objective 232 is an air-gap, long-working-distance, infinity-corrected achromatic objective.

Referring to FIGS. 2, 5A to 5C, and 6, a typical sequence of events is described comprising interrogation of particles under analysis in the method according to an embodiment of the present invention. At the time of FIG. 5A, representative particle 510 is yet to reach the region where interaction with any of the laser beams is to take place. At the time of FIG. 5B, particle 510 has reached the region of interaction with cw beam 231'; the result of that interaction, represented by trigger beam 235', is used as a trigger signal that ultimately results in combined pump-Stokes pulse beam 233' interrogating particle 510 at the time of FIG. 5C. The time interval $t_{b-c}$ that elapses between the time of FIG. 5B and that of FIG. 5C depends on the distance $d_{b-c}$ between focused cw beam spot 231" and focused combined pump-Stokes beam spot 233" in the focal plane of microscope objective 226 in flow channel 228", and on the velocity $v_{particle}$ of particle flow in the flow channel. Both such distance $d_{b-c}$ and such velocity $v_{particle}$ can be adjusted within a range of practically achievable values; their design values are set to result in a time interval $t_{b-c}$ sufficiently long to allow for the propagation of optical and electrical signals through the apparatus. For the purpose of adjusting $v_{particle}$, the effective rate of injection of sheath and carrier fluids 506 into flow channel 228" is adjusted. For the purpose of adjusting $d_{b-c}$, dichroic mirror 222 is aligned and oriented to direct cw beam 229 through microscope objective 226 and into flowcell 240" in such a way as to place focused cw beam spot 231" upstream (with respect to the direction of fluid flow in flow channel 228" shown by vector 508) from focused combined pump-Stokes beam spot 233". Distance $d_{b-c}$ is designed to be such that the time interval $t_{b-c}$ it takes a particle to traverse it closely approximates the cumulative time it takes for a signal (optical or electrical as respectively relevant) to propagate along the path comprising segments 235, 239, 241, 243, 245, 247, 201, 205, 207, 209, 211, 213, 219, 221, 223, and 233, plus any significant internal delay in intervening components, including 504, 232, 236, 238, 260, 210, 206, 208, 216, 218, 222, 226, and 502. Synchronization control module 270 is used during operation to calibrate such interval $t_{b-c}$ and make any necessary residual adjustments in the timely generation of synchronization trigger signal 247, to so that combined pump-Stokes pulse beam 233' arrives at the flow channel at the time particle 510 is passing through the region where such pulse will intersect it.

Synchronization system 270 comprises sufficiently fast electronic circuitry with sufficiently low timing noise, or jitter, to enable faithful generation of electrical gating signal 259, synchronization trigger signal 247, and electronic time stamp signal 249 in response to electrical trigger signal 245 without introducing unacceptable amounts of temporal spread or distortion.

Data acquisition module 280 is a multichannel digitization and signal processing module. It is set up to acquire input signals from photodetector 238, photodetector 252, synchronization control module 270, and photodetector array 260, and to exchange control signals and processed data with computer module 290. Photodetector array 260 produces coded anti-Stokes spectral signal 261 at a rate generally limited by the maximum repetition rate of ultrafast amplifier module 210. Coded anti-Stokes spectral signal 261 is acquired by data acquisition module 280 and digitally associated therein with electrical trigger signal 245, altered pump pulse electrical signal 267, and electronic time stamp signal 249, all of these signals being mutually synchronized up to a fixed and calibratable time offset. Data acquisition module 280 digitizes analog input waveforms at a sufficient digitization frequency to faithfully record signal variations from the respective sources, performs signal buffering, and associates into a discrete data packet all of the signals pertaining to an individual particle analysis event, further transmitting one such data packet per particle analysis event to computer module 290.

Computer module 290 provides a user interface with which to control user-adjustable parameters of operation of particle analysis apparatus 200 according to the method according to an embodiment of the present invention, and to direct such apparatus to perform a particle analysis according to such method. Computer module 290 further provides means to process and store particle analysis data transferred to it by data acquisition module 280, and means to optionally view, analyze, and transfer such data to long-term storage systems. Spectral information obtained on apparatus 200 using the method in accordance with an embodiment of the present invention may be analyzed in various ways known in the art, such as, e.g., by comparison, differencing, overlay, or otherwise correlative inspection of recorded spectra from particles under analysis with one or more spectra of known substances or particles; by quantification of individual spectral features, such as, e.g., the presence, or height over background, or width, or shape, of one or more spectral peaks; by principal component analysis; or by other such spectral analysis procedures.

Figure 7:
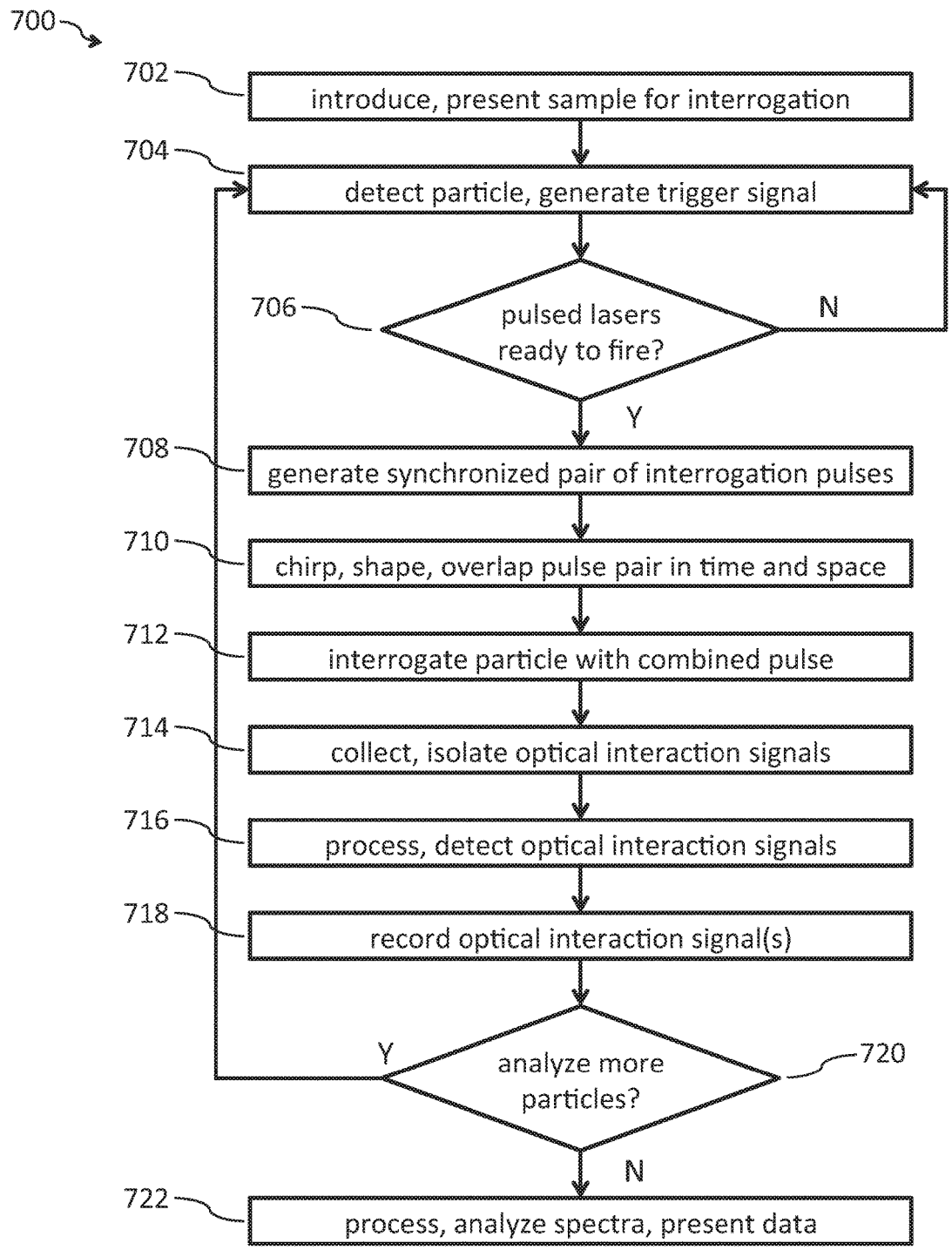
FIG. 7 is a flow chart describing a sequence of principal operations involved in the performance of the method of particle analysis in accordance with one embodiment.

Referring to FIG. 7, a flow chart 700 is provided that describes a sequence of principal operations involved in the performance of the method of particle analysis in accordance with an embodiment of the present invention. At a method operation 702, a user or operator of apparatus 200 introduces into apparatus 200 a sample containing a plurality of particles for analysis; apparatus 200 aspirates, aliquots, or otherwise isolates a portion or a totality of such sample for optical interrogation; such portion or totality is injected, as a particle-carrying carrier fluid and in conjunction with the simultaneous injection of sheath fluid, into flow channel 228 within flowcell 240, thereby forming a core sample stream bounded by sheath fluid and progressing in the direction of vector 508; such core sample stream carries particles to interrogation region 500 where they are presented for optical interrogation.

At a method operation 704, a particle 510 of the plurality of particles in the sample enters cw beam 231' with wavelength 402; a transient optical signal in the form of trigger beam 235' is generated as a result of the passage of particle 510 in cw beam 231'; such transient optical signal is collected by microscope objective 232, reflects off dichroic mirror 234, is isolated by undesired light of other wavelengths by filter 236, and is converted by photodetector 238 into electrical trigger signal 245; electrical trigger signal 245 is received by synchronization control module 270 and used to generate synchronization trigger signal 247 and electronic time stamp signal 249.

At a method operation 706, ultrafast amplifier module 210 receives synchronization trigger signal 247; timing electronic circuitry and control firmware internal to ultrafast amplifier module 210 verify whether ultrafast amplifier module 210 is ready to produce the desired ultrafast output pulse, based on the minimum pulse-repetition period of ultrafast amplifier module 210; if the result of such verification is negative, the process is repeated starting with method operation 704; if the result is positive, a next method operation 708 is taken.

At method operation 708, ultrafast amplifier module 210 generates a single pulse with Stokes band 408; beamsplitter 202 transmits part of the intensity of such pulse to OPA 220 and reflects the rest through mirror 204 to dispersion control module 206; OPA 220 generates a single pulse with pump band 406 synchronized to the pulse from ultrafast amplifier 210.

At a method operation 710, the pulse from OPA 220 is positively chirped as ellipse 356 by dispersion control module 214 and sent as a pump pulse of pump pulse beam 217 to dichroic mirror 216; the pulse from ultrafast amplifier 210 is negatively chirped as ellipse 352 by dispersion control module 206, delayed by variable delay line 208, and reflected by mirror 212 as a Stokes pulse of Stokes pulse beam 213 to dichroic mirror 216, where it combines with the pump pulse in time and space as a combined pulse of combined pump-Stokes pulse beam 219; the combined pulse is altered in spatial dimensions by beam shaper 218, passes through dichroic mirror 222, enters microscope objective 226, and is focused through top flowcell wall 502 and through portion of sheath and carrier fluids 506 into flow channel 228' as a combined pulse of combined pump-Stokes pulse beam 233'.

At a method operation 712, the combined pulse interrogates particle 510 by optical processes comprising inelastic light scattering, such as, e.g., Coherent anti-Stokes Raman Scattering (CARS); an anti-Stokes light signal is generated as ellipse 364 with anti-Stokes band 404, the forward-propagating portion of which combines with the interrogating combined cross-chirped pulse pair to form a combined CARS pulse of combined CARS pulse beam 237'.

At a method operation 714, the combined CARS pulse propagates through portion of sheath and carrier fluids 506, propagates through bottom flowcell wall 504, is collected by microscope objective 232, and passes through dichroic mirror 234 to reach dichroic mirror 242; the combined CARS pulse is then separated into the anti-Stokes signal portion, which is reflected through spectral filter 244 to spectrometer 250, and the combined pump-Stokes portion, which reaches spectral filter 246; the Stokes portion of the combined pump-Stokes portion is rejected by spectral filter 246; the pump portion is transmitted by spectral filter 246, attenuated by neutral-density filter 248, and reaches photodetector 252.

At a method operation 716, synchronization control module 270 generates electrical gating signal 259 and transmits it to photodetector array 260; the anti-Stokes signal is dispersed by spectrometer 250 into an anti-Stokes spectrum transmitted to photodetector array 260; photodetector array 260 integrates the optical spectrum incident upon it for the duration of electrical gating signal 259, which is timed to synchronize with the anti-Stokes signal; photodetector array 260 converts the anti-Stokes spectrum received from spectrometer 250 into coded anti-Stokes spectral signal 261; photodetector 252 converts the pump portion of the combined CARS pulse into altered pump pulse electrical signal 267.

At a method operation 718, data acquisition module 280 receives, at various time delays with respect to the passage of particle 510 through cw beam 231', electrical trigger signal 245, electronic time stamp signal 249, coded anti-Stokes spectral signal 261, and altered pump pulse electrical signal 267; data acquisition module 280 converts any analog signals received into digitized equivalents; data acquisition module 280 optionally processes such received and digitized signals to improve their signal-to-noise characteristics; data acquisition module 280 provides for a temporary storage of the received and digitized signals as associated items in a digital packet identified by its time stamp on an onboard memory module; data acquisition module 280 optionally transmits such digital packet to computer module 290 for further preliminary processing.

At a method operation 720, a firmware function determines, on the basis of user-defined parameters and default parameters (such as, for example and without limitation, the number of individual particle spectra collected from the sample being analyzed; the number such spectra satisfying predetermined criteria; the time elapsed since the sample was introduced; the interruption by the user or operator), whether apparatus 200 should be directed to analyze yet more particles; if the result of such determination is positive, the analysis process is repeated starting with method operation 704; if the result is positive, a next method operation 722 is taken. At method operation 720, another firmware function periodically directs apparatus 200 to collect background spectra from the carrier fluids in the absence of particles for use in background subtraction and other signal processing functions.

At method operation 722, digital packets corresponding to each recorded particle-interrogation event since the sample was introduced for analysis, plus digital packets corresponding to background spectra, are transmitted from data acquisition module 280 to computer module 290; computer module 290 performs digital signal processing and data analysis functions on such packets, such as, for example without limitation, background subtraction, smoothing, upsampling, Fourier filtering, noise filtering, baseline subtraction, peak detection, normalization, averaging, weighted averaging, signal differencing, comparison to libraries, comparison to look-up tables, feature extraction, principal component analysis, support vector machine analysis, Bayesian analysis, and/or other spectral processing and analysis functions as are known in the art; computer module 290 further stores the results of such processing and analysis, individually and/or in aggregate; computer module 290 optionally presents such results to the user or operator via a user interface, or optionally transmits such results to a separate unit for long-term storage, aggregation, and/or further analysis.

In an embodiment, the trigger functions (trigger beam, trigger detector, electrical trigger signal, synchronization trigger signal) are not needed to analyze particles the concentration of which is substantially high. The combined CARS pulses are generated periodically to interrogate the particle as described for example, in operation 712, and are unsynchronized with the passage of particles in the flow channel. Synchronization is retained between the combined CARS pulses and the electrical gating signal for the photodetector array. The volumetric concentration of particles in the core sample stream is arranged to be sufficiently high so that each combined CARS pulse has a correspondingly sufficiently high probability of interacting with a particle in the sample stream. For a pulse repetition rate of, for example, 5 kHz, and an interaction probability of, for example, 10%, the effective resulting average event interaction is 500 particles per second.

In another embodiment, the trigger functions (trigger beam, trigger detector, electrical trigger signal, synchronization trigger signal) are not needed to analyze fluids (such as, e.g., pure fluids, mixtures, solutions, suspensions, multi-phase fluids, etc.), as described in further detail below. For example, the fluid may be a solution of one or more solute analyte compounds dissolved in a solvent. The combined CARS pulses are generated periodically to interrogate fluids in a manner similar to that described, for example, in operation 712, and are free-running with respect to the passage of fluid(s) in the flow channel. Synchronization is retained between the combined CARS pulses and the electrical gating signal for the photodetector array. Each combined CARS pulse interrogates a volumetric portion of the fluid(s) presented for analysis, and the collection of multiple spectra from a plurality of combined CARS pulses yields an overall assay of the fluid(s) presented for analysis. The spectral signals resulting from the interaction of the combined pulse with the fluid(s) are separated from the background noise, collected, and processed, for example as described with respect to operation 716. For a pulse repetition rate of, for example, 1 kHz, 1,000 CARS spectra per second are acquired from the fluid(s) under analysis.

In another embodiment, the trigger functions (trigger beam, trigger detector, electrical trigger signal, synchronization trigger signal) are not needed, and laser oscillators replace the laser amplifiers, to analyze fluids (such as, e.g., pure fluids, solutions, mixtures, suspensions, multi-phase fluids, etc.), as described in further detail below. For example, the fluid may be a solution of one or more solute analyte compounds dissolved in a solvent. The combined CARS pulses from two laser oscillators operating at different wavelengths are generated periodically to interrogate fluids in a manner similar to that described, for example, in operation 712, and are free-running with respect to the passage of fluid(s) in the flow channel. Each combined CARS pulse interrogates a volumetric portion of the fluid(s) presented for analysis, and the accumulation of multiple spectra from a plurality of combined CARS pulses yields an overall analysis of the fluid(s) presented for analysis. The signals resulting from the interaction of the combined pulse with the fluid(s) are separated from the background noise, collected, and processed, for example as described with respect to operation 716. The photodetector array is optionally arranged to integrate multiple CARS spectra and generate an aggregate signal. For a pulse repetition rate of, for example, 100 MHz, and an integration time of 1 ms, 1,000 integrated spectra per second are recorded, each spectrum integrating approximately 100,000 individual interactions between combined CARS pulses and portions of the fluid(s) under analysis.

EXAMPLES

An example of the embodiment with values of the main parameters of operation is provided herein. For simplicity of illustration, three separate selections of wavelength tuning ("Selection A", "Selection B", and "Selection C") are offered as possible instances, without limitation, of different settings for the same apparatus according to an embodiment.

Referring to Table 1, for each column corresponding to a different wavelength tuning selection, center wavelength ($<\lambda>$, in nm), corresponding center wavenumber ($<\omega>$, in $cm^{-1}$), pulse duration ($\Delta\tau$, in fs), and bandwidth ($\Delta\omega$, in $cm^{-1}$) are each shown for pulse beam 201 from ultrafast amplifier module 210 (underscript "amp"); for Stokes pulse beam 209 after chirping by dispersion control module 206 (underscript "Stokes"); for pulse beam 215 from OPA 220 (underscript "OPA"); and for pump pulse beam 217 after chirping by dispersion control module 214 (underscript "pump"). Table 1 additionally shows center wavelength and corresponding center wavenumber for anti-Stokes signal pulse beam 257 (underscript "anti-Stokes"); and the approximate range of Raman transitions (indicated by the low 50% point, $\Omega_{Raman}$ low, and the high 50% point, $\Omega_{Raman}$ high) accessible for each wavelength tuning selection. Quantities such as $\Delta\tau$ and $\Delta\omega$ indicate the approximate Full-Width at Half-Maximum (FWHM) values of the respective temporal and wavenumber profiles of the pulses they describe. Likewise, $\Omega_{Raman}$ low and $\Omega_{Raman}$ high indicate the two points approximately at half-maximum of the anti-Stokes bandwidth profile.

TABLE 1

Example of operating parameters with three choices of OPA tuning wavelength.

| Quantity | Selection A | Selection B | Selection C | units |
|---|---|---|---|---|
| $<\lambda_{amp}>$ | 800 | 800 | 800 | nm |
| $<\omega_{amp}>$ | 12,500 | 12,500 | 12,500 | $cm^{-1}$ |
| $\Delta\tau_{amp}$ | 40 | 40 | 40 | fs |
| $\Delta\omega_{amp}$ | 367 | 367 | 367 | $cm^{-1}$ |
| $<\lambda_{Stokes}>$ | 800 | 800 | 800 | nm |
| $<\omega_{Stokes}>$ | 12,500 | 12,500 | 12,500 | $cm^{-1}$ |
| $\Delta\tau'_{Stokes}$ | 5 | 5 | 5 | ps |
| $\Delta\omega_{Stokes}$ | 367 | 367 | 367 | $cm^{-1}$ |
| $<\lambda_{OPA}>$ | 733 | 685 | 643 | nm |
| $<\omega_{OPA}>$ | 13,643 | 14,599 | 15,552 | $cm^{-1}$ |
| $\Delta\tau_{OPA}$ | 40 | 40 | 40 | fs |
| $\Delta\omega_{OPA}$ | 367 | 367 | 367 | $cm^{-1}$ |
| $<\lambda_{pump}>$ | 733 | 685 | 643 | nm |
| $<\omega_{pump}>$ | 13,643 | 14,599 | 15,552 | $cm^{-1}$ |
| $\Delta\tau'_{pump}$ | 5 | 5 | 5 | ps |
| $\Delta\omega_{pump}$ | 367 | 367 | 367 | $cm^{-1}$ |
| $<\lambda_{anti-Stokes}>$ | 676 | 599 | 538 | nm |
| $<\omega_{anti-Stokes}>$ | 14,785 | 16,697 | 18,604 | $cm^{-1}$ |
| $\Omega_{Raman}$ low | 593 | 1,549 | 2,502 | $cm^{-1}$ |
| $\Omega_{Raman}$ high | 1,693 | 2,649 | 3,602 | $cm^{-1}$ |

It will be noted that, insofar as the parameters reported in Table 1 are concerned, the only difference between the characteristics of pulse beam "amp" and pulse beam "Stokes" is the temporal width, due to chirping. Likewise, the only difference between the characteristics of pulse beam "OPA" and pulse beam "pump" is the temporal width, again due to chirping. Accordingly, the bandwidth shown for pulse beams "amp" and "OPA" is the transform-limited value corresponding to their pulse durations; whereas the bandwidth shown for pulse beams "Stokes" and "pump" is the bandwidth each of them inherits from pulse beams "amp" and "OPA," respectively.

In this example of the embodiment, ultrafast amplifier module 210 comprises an ultrafast oscillator and a Chirped Pulse Amplification-based Ti:sapphire regenerative amplifier tuned to a center wavelength of approximately 800 nm, as well as the required pump lasers and supporting components. A commercially available laser system suitable for use as ultrafast amplifier module 210 is the Libra-HE+ USP model (Coherent, Santa Clara, Calif., USA). Ultrafast amplifier module 210 is set to produce output pulses at a rate dictated by the arrival of particles for analysis, with an upper bound given by the maximum repetition rate of ultrafast amplifier module 210 (such repetition rate is, for example, in the approximate range of 1 Hz to 1 MHz, in the approximate range of 100 Hz to 100 kHz, and in more specific embodiment, in the approximate range of 1 to 10 kHz). The energy per pulse for pulse beam 201 from ultrafast amplifier module 210 is, for example, in the approximate range of 1 µJ to 100 mJ, in the approximate range of 100 µJ to 25 mJ, and in more specific embodiment, in the approximate range of 1 mJ to 5 mJ, with beamsplitter 202 selecting approximately 90% of the pulse energy for transmission as pulse beam 203 and reflecting the remaining 10% as pulse beam 205. OPA 220 is set to deliver the second harmonic of the nonlinear frequency conversion signal at a center wavelength, given an input pulse beam 203 at a wavelength of 800 nm, generally tunable from below 600 nm to about 800 nm. (Other choices of signal output from OPA 220 are possible, resulting in tuning over different wavelength ranges both above and below the wavelength of input pulse beam 203.) A commercially available optical parametric amplifier system suitable for use as OPA 220 is the TOPAS model (Coherent, Santa Clara, Calif., USA). Referring to Table 1, for wavelength tuning selection A, OPA 220 is tuned to a center wavelength of about 733 nm, resulting in an energy per pulse for pulse beam 215 of about 160 µJ (assuming a 3.5 mJ input pulse at 800 nm); for selection B, OPA 220 center wavelength is about 685 nm and the pulse energy about 220 µJ; for selection C, OPA 220 center wavelength is about 643 nm and the pulse energy about 240 µJ. The bandwidth of the "amp," "Stokes," "OPA," and "pump" pulses is approximately the same and equal to approximately 367 $cm^{-1}$. The bandwidth of the "anti-Stokes" pulse is the result of the CARS frequency-mixing process and is approximately equal to 1,100 $cm^{-1}$.

With the operating parameter choices indicated in Table 1, the apparatus according to an embodiment of the present invention is capable of performing particle analysis by single-shot CARS spectroscopy over a broad range of Raman transitions. With wavelength tuning selection A, the approximate range of Raman transitions covered is 600 to 1700 $cm^{-1}$; with selection B, the approximate range is 1,550 to 2,650 $cm^{-1}$; with selection C, the approximate range is 2,500 to 3,600 $cm^{-1}$. Selection A covers the region of the Raman spectrum commonly known as the fingerprint region; selection C covers the region of the Raman spectrum featuring prominent lipid and water peaks; and selection B covers the region of the spectrum lying in between the fingerprint region and the lipid/water peaks. The spectral range for selection B partially overlaps with the spectral ranges of both selection A and selection C to facilitate spectral calibration across the combined range of approximately 600 to approximately 3,600 $cm^{-1}$.

In this example of the embodiment, cw source 230 produces a beam with a center wavelength of approximately 488 nm and a power in the approximate range of 1 to 100 mW, and in more specific embodiment, in the approximate range of 5 to 25 mW. The cross-sectional dimension of flow channel 228 in the direction parallel to light propagation is, for example, in the approximate range of 50 to 1000 µm, in the approximate range of 100 to 500 µm, and in more specific embodiment in the approximate range of 200 to 300 µm. The cross-sectional dimension of flow channel 228 in the direction perpendicular to light propagation is, for example, in the approximate range of 50 to 1000 µm, in the approximate range of 100 to 500 µm, and in more specific embodiment, in the approximate range of 200 to 300 μm. The velocity of carrier fluid and particles in the center of the channel along vector 508 is, for example, in the approximate range of 0.01 to 50 m/s, in the approximate range of 0.1 to 20 m/s, and in more specific embodiment, in the range of 1 to 10 m/s. The approximate dimensions of focused cw beam spot 231" are 10 μm in the direction of vector 508 and 80 μm in the direction perpendicular to vector 508. The approximate dimensions of focused combined pump-Stokes beam spot 233" are 0.6 μm in the direction of vector 508 and 10 μm in the direction perpendicular to vector 508. Particles to be analyzed are, for example, in the approximate range of 50 nm to 50 μm, in the approximate range of 500 nm to 20 μm, and in more specific embodiment, in the approximate range of 1 to 10 μm. Electrical gating signal 259 has a duration greater than the duration of stretched pulse duration Δτ' and, for example less than 100 μs, less than 100 ns, and in more specific embodiment, less than 500 ps; and is synchronized to bracket stretched pulse duration Δτ'. Spectrometer 250 has, for example an approximate spectral resolution of better than about 20 cm$^{-1}$, better than about 10 cm$^{-1}$, and in more specific embodiment, better than about 5 cm$^{-1}$.

It will be apparent from the foregoing description that the method and apparatus of embodiments of the present invention offer means to carry out particle analyses rapidly, with sensitivity to chemical composition, over ensembles of large numbers of particles, and without the use of expensive reagents. While the foregoing description contains many specificities, these should not be construed as limitations on the scope of the invention, but rather as an exemplification of one embodiment thereof. Many other variations are possible. For example:

1) An alternative embodiment where variable delay line is removed from the path between pulse beams 209 and 211 and inserted instead in the path of pulse beam 217 in order to satisfy the requirement for temporal overlap of pump and Stokes pulse beams given a specific beam path geometry, component layout, and internal delays. An alternative embodiment where OPA 220 is tuned to a wavelength longer than that produced by ultrafast amplifier 210; where the roles of ultrafast amplifier module 210 and OPA 220 are thereby reversed in the CARS process, i.e., pulse beam 217 acts as the Stokes beam and pulse beam 213 acts as the pump beam; and where longpass dichroic mirror 216 is replaced by a shortpass dichroic mirror with an edge wavelength in between the center wavelengths of ultrafast amplifier 210 and OPA 220.

2) An alternative embodiment where ultrafast amplifier module 210 comprises any of a fixed-wavelength fiber-based ultrafast pulsed laser oscillator, a fixed-wavelength free-space ultrafast pulsed laser oscillator, a fiber-based pump laser for the oscillator, a fixed-wavelength fiber-based amplifier, a fixed-wavelength free-space amplifier, a fiber-based pump laser for the amplifier, a single-pass amplifier stage, a multi-pass amplifier stage, or any suitable combination thereof.

Figure 8:
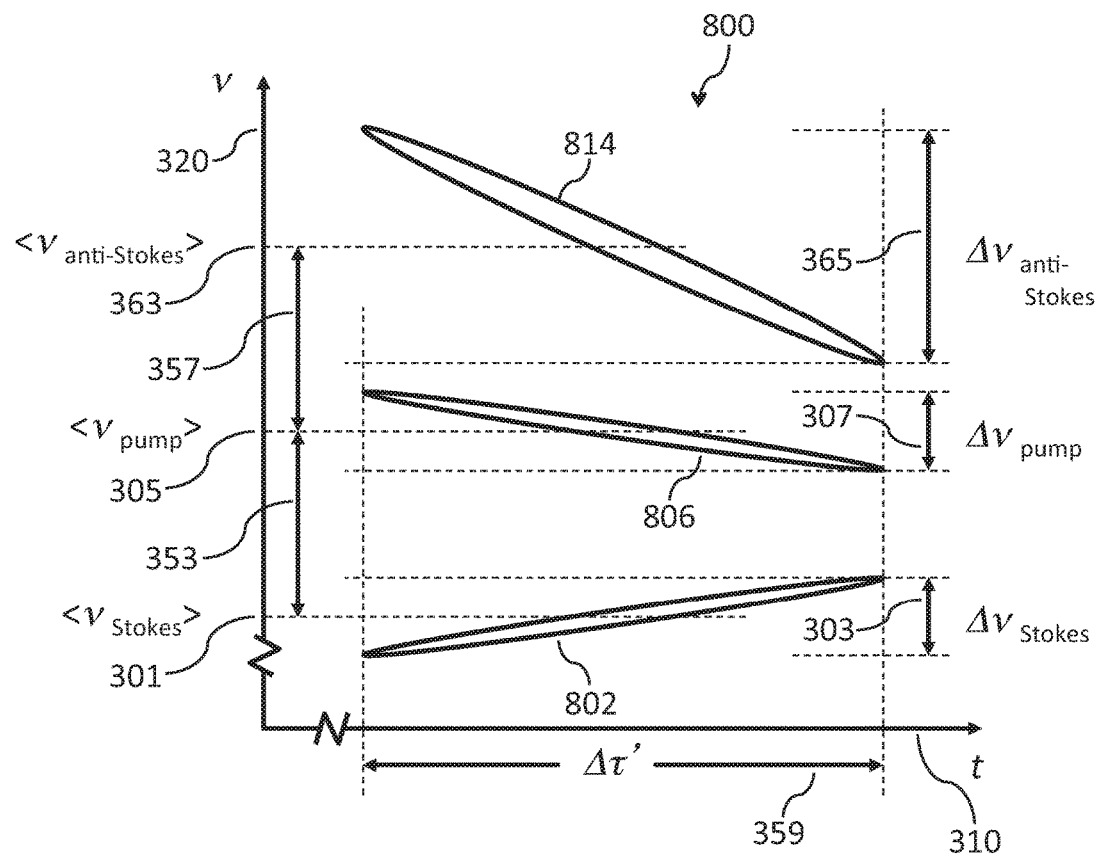
FIG. 8 illustrates a spectroscopic method to be performed in accordance with one embodiment.

3) Referring to FIGS. 2 and 8, an alternative embodiment where dispersion control module 206 is designed to impart a positive chirp, e.g., by comprising a length of material with positive Group Velocity Dispersion; where the resulting Stokes pulse beam 209 is represented in FIG. 8 on frequency-time graph 800 as a Stokes ellipse 802; where dispersion control module 214 is designed to impart a negative chirp, e.g., by comprising a pulse compressor arrangement of matched prisms or matched gratings with overall anomalous dispersion characteristics; where the resulting pump beam 217 is represented in FIG. 8 as a pump ellipse 806; and where the anti-Stokes portion of combined CARS pulse beam 237 is represented in FIG. 8 as an anti-Stokes ellipse 814. An alternative embodiment where settings internal to ultrafast amplifier module 210 are used to generate a negatively chirped pulse with the desired characteristics, i.e., a temporally stretched pulse; and where dispersion control module 206 is removed.

4) An alternative embodiment where settings internal to OPA 220 are used to generate a positively chirped pulse with the desired characteristics, i.e., a temporally stretched pulse; and where dispersion control module 214 is removed.

5) An alternative embodiment where OPA 220 is replaced by a second ultrafast amplifier module, e.g., a module similar to ultrafast amplifier 210; where both ultrafast amplifier module 210 and such second module produce, or are tuned to, wavelengths suitable for performing the method according to an embodiment of the present invention; and where ultrafast amplifier module 210 and such second module are mutually synchronized by means of synchronization electronics including but not necessarily limited to synchronization control module 270.

Figure 9:
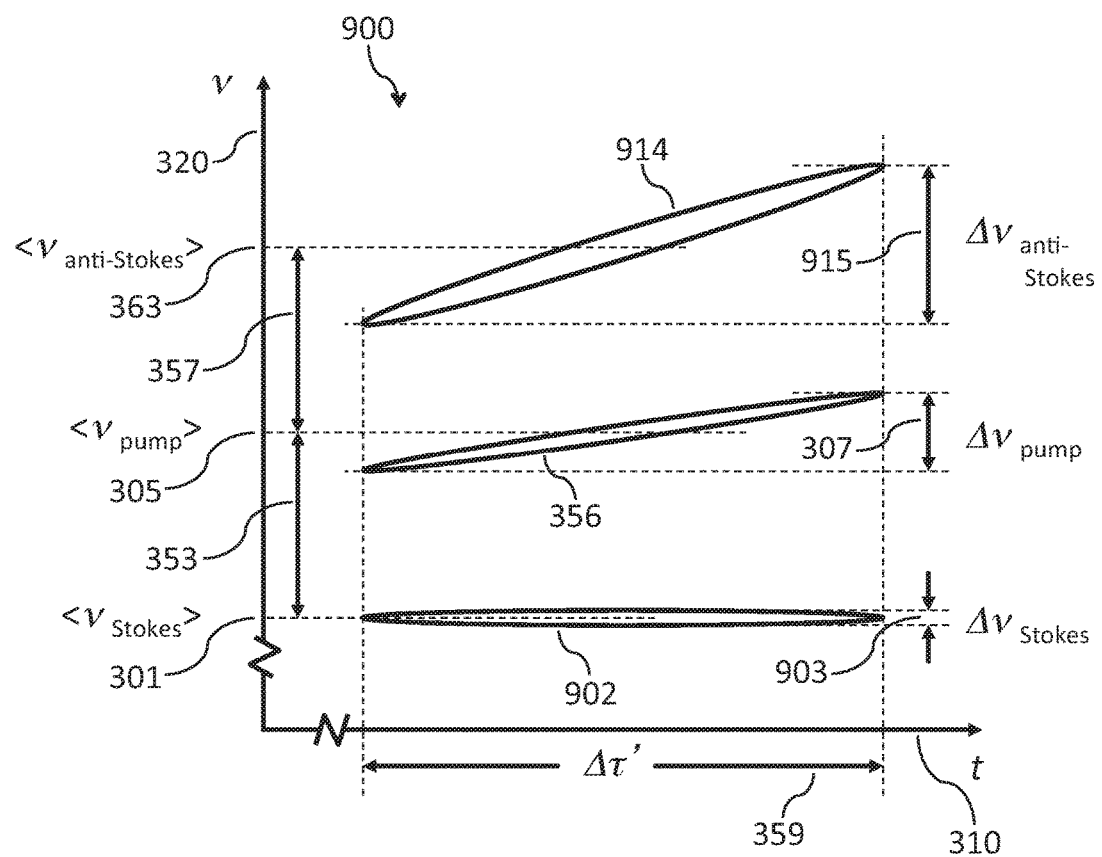
FIG. 9 illustrates a spectroscopic method to be performed in accordance with one embodiment.

6) Referring to FIGS. 2 and 9, an alternative embodiment incorporating the changes of alternative embodiment (5); where, additionally, dispersion control module 206 is removed; where ultrafast amplifier module 210 is set to produce transform-limited picosecond-duration pulses; where the resulting Stokes pulse beam 209 is represented in FIG. 9 on frequency-time graph 900 as a Stokes ellipse 902; and where the anti-Stokes portion of combined CARS pulse beam 237 is represented in FIG. 9 as an anti-Stokes ellipse 914 having anti-Stokes bandwidth $\Delta v_{anti-stokes}$ 915. An alternative embodiment where longpass dichroic mirrors 216, 222, 234, 242, or any combination thereof, are replaced by shortpass analogues with similar respective edge wavelengths; and where the geometry of affected beam paths and the layout of affected components are adjusted accordingly.

7) An alternative embodiment where shortpass filters 236, 244, 246, or any combination thereof, are supplemented by bandpass filters with acceptable transmission values over the respective wavelengths or wavelength bands 402, 404, and 406 and acceptable extinction values over other wavelength ranges containing undesired signals.

8) An alternative embodiment incorporating the changes of alternative embodiment (7); and where, additionally, shortpass filters 236, 244, 246, or any combination thereof, are removed.

9) An alternative embodiment where shortpass filter 236 is supplemented by a notch filter with high extinction over band 406 and with acceptable transmission at wavelength 402, a notch filter with high extinction over band 408 and with acceptable transmission at wavelength 402, or both such notch filters.

10) An alternative embodiment where shortpass filter 244 is supplemented by a notch filter with high extinction at wavelength 402 and with acceptable transmission over band 404, a notch filter with high extinction over band 406 and with acceptable transmission over band 404, a notch filter with high extinction over band 408 and with acceptable transmission over band 404, or any combination thereof.

11) An alternative embodiment where shortpass filter 246 is supplemented by a notch filter with high extinction at wavelength 402 and with acceptable transmission over band 406, a notch filter with high extinction over band 408 and with acceptable transmission over band 406, or both such notch filters.

12) An alternative embodiment where cw source 230 is directed onto the particles under analysis in flow channel 228 by means of an optical path propagating separately from combined pump-Stokes pulse beams 223 and 233 and not passing through microscope objectives 226 and 232; where an additional focusing lens is placed between beam shaper 224 and flowcell 240 to obtain the desired focused cw beam spot dimensions; where an additional collection lens is placed between flowcell 240 and spectral filter 236; where dichroic mirrors 222 and 234 are removed; and where the beam path from cw source 230 to photodetector 238 proceeds through beam shaper 224, said additional focusing lens, flowcell 240, flow channel 228, said additional collection lens, and spectral filter 236.

13) An alternative embodiment where cw source 230 comprises a laser with an output wavelength of value within the approximate range of 200 nm to 5000 nm; and where such wavelength is sufficiently shorter than the shortest wavelength in anti-Stokes band 404 to prevent interference with or from the CARS signal.

14) An alternative embodiment where cw source 230 comprises an LED, a superluminescent LED, or other incoherent light source, optionally suitably filtered, with an output band having a center wavelength within the approximate range of 200 nm to 5000 nm; and where the longest wavelength in such output band is sufficiently shorter than the shortest wavelength in anti-Stokes band 404 to prevent interference with or from the CARS signal.

15) An alternative embodiment where longpass dichroic mirrors 222 and 234 are replaced by shortpass dichroic mirrors having an edge wavelength longer than the longest wavelength in Stokes band 408; where shortpass spectral filter 236 is replaced by a longpass spectral filter with a similar edge wavelength to that of said shortpass dichroic mirrors; where cw source 230 comprises a laser with an output wavelength of value within the approximate range of 355 nm to 1700 nm; and where the wavelength of cw source 230 is sufficiently longer than the edge wavelength of said shortpass dichroic mirrors to prevent interference with or from the Stokes beam.

16) An alternative embodiment where longpass dichroic mirrors 222 and 234 are replaced by shortpass dichroic mirrors having an edge wavelength longer than the longest wavelength in Stokes band 408; where shortpass spectral filter 236 is replaced by a longpass spectral filter with a similar edge wavelength to that of said shortpass dichroic mirrors; where cw source 230 comprises an LED, a superluminescent LED, or other incoherent light source, optionally suitably filtered, with an output band having a center wavelength within the approximate range of 200 nm to 5000 nm; and where the shortest wavelength of cw source 230 is sufficiently longer than the edge wavelength of said shortpass dichroic mirrors to prevent interference with or from the Stokes beam.

17) An alternative embodiment where beam shaper 218 is designed to produce, in conjunction with microscope objective 226, a focused combined pump-Stokes beam spot 233" with approximately equal dimensions in the directions parallel to and perpendicular to vector 508; and where such dimensions are, for example, in the approximate range of 0.2 to 20 μm, in the approximate range of 0.5 to 10 μm, and in more specific embodiment, in the approximate range of 1 to 5 μm.

18) An alternative embodiment where dichroic mirror 242 is removed from its location between dichroic mirror 234 and spectral filter 246, and placed in the path of beam 221 between beam shaper 218 and dichroic mirror 222; where such repositioned dichroic mirror 242 is oriented to reflect light below its edge wavelength 405 away from beam 221 and toward an accessible direction; where spectral filter 244 and spectrometer 250 with associated photodetector array 260 are suitably repositioned to receive light reflected by such repositioned dichroic mirror 242; and where any anti-Stokes signal light backpropagating along beam 221 from the interaction region in flowcell 240 is thusly reflected by such repositioned dichroic mirror 242, filtered by such repositioned spectral filter 244, and measured by repositioned spectrometer 250 and photodetector array 260.

Figure 10:
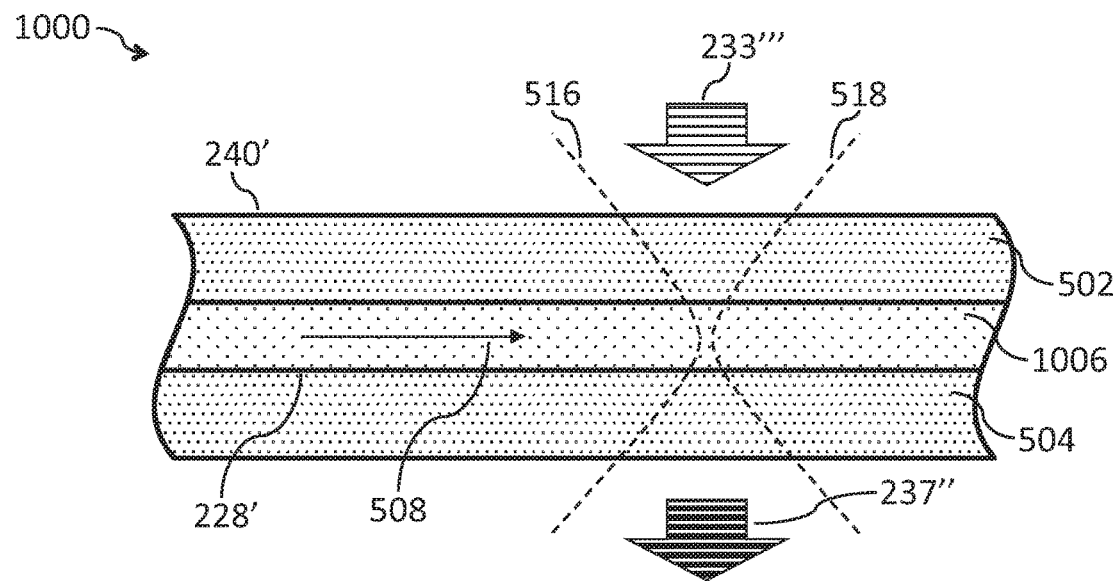
FIG. 10 is a schematic representation of aspects of sample analysis in accordance with one embodiment.

19) Referring to FIGS. 2, 5(*c*) and 10, an alternative embodiment where the following elements are removed: 230, 224, 222, 234, 236, 238, 246, 248, 252; where ultrafast amplifier module 210 and OPA 220 are each replaced by a mode-locked ultrafast laser oscillator; where each such mode-locked ultrafast laser oscillator is tuned to a wavelength suitable for performing the method according to an embodiment of the present invention; where each such mode-locked ultrafast laser oscillator produces a continuous train of transform-limited, femtosecond-scale-duration, nanojoule-scale-energy pulses at repetition rates, for example, in the approximate range of 1 MHz to 1 GHz, and, in more specific embodiment, in the approximate range of 10 MHz to 100 MHz; where such mode-locked ultrafast laser oscillators are mutually synchronized by means of synchronization electronics including but not necessarily limited to synchronization control module 270; where, referring to an interrogation region 1000 in FIG. 10, sheath fluid and particle-carrying carrier fluid 506 are replaced by a fluid 1006 under analysis; where fluid 1006 may comprise, e.g., a single fluid of known or unknown composition, a solution with one or more unknown solutes, a solution with an unknown concentration of one or more known solutes, a mixture of one or more unknown fluids, a mixture with an unknown concentration of one or more known fluids, a suspension with one or more populations of unknown solid components, a suspension with an unknown concentration of one or more known solid components, a multi-phase medium (including, but not limited to, emulsions and aerosols) with two or more unknown phases, a multi-phase medium (including, but not limited to, emulsions and aerosols) with an unknown ratio of two or more known phases, or any combination thereof; where a combined pump-Stokes pulse train 233''' is designed to focus inside flow channel 228', interrogate a volume of fluid 1006, and produce by such interrogation a combined CARS pulse train 237"; where and where electrical gating signal 259 is modified to permit accumulation and integration in photodetector array 260 of dispersed spectra from a plurality of individual interrogation events.

It will be apparent to someone skilled in the art that many of the foregoing alternative embodiments may be usefully combined to produce yet other distinct alternative embodiments. For example, alternative embodiments (3), (3), (4), and (5) may be combined to result in another alternative embodiment comprising two ultrafast amplifier modules, not comprising either dispersion control module 206 or dispersion control module 214, and capable of performing the spectroscopic method illustrated in FIG. 8. Accordingly, the scope of the invention should be determined not by the embodiments illustrated, but by the appended claims and their legal equivalents.

Figure 11:
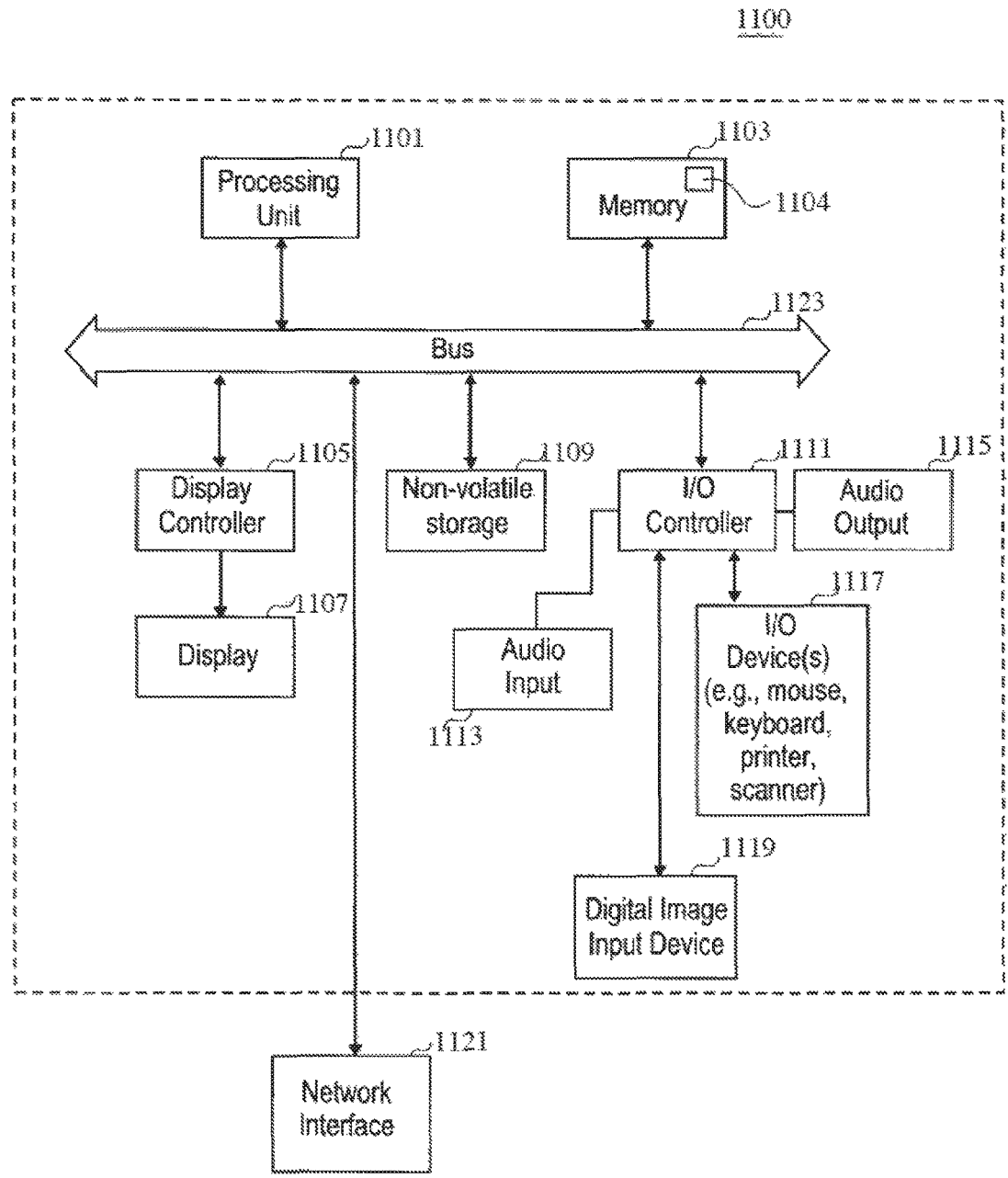
FIG. 11 shows a block diagram of an exemplary embodiment of a data processing system to analyze particles as described herein.

FIG. 11 shows a block diagram of an exemplary embodiment of a data processing system 1100 to provide a label-free or native particle analysis as described herein. In an embodiment, data processing system 1100 is a part of the control system to perform a method that includes generating first light pulses at a first wavelength; generating second light pulses at a second wavelength; conveyed particles for analysis, where least one of the first light pulses and the second light pulses is chirped to analyze the particles, as described herein. In an embodiment, data processing system 1100 is represented by a computer module 290 depicted in FIG. 2.

Data processing system 1100 includes a processing unit 1101 that may include a microprocessor or microprocessor, such as Intel microprocessor (e.g., Core i7, Core 2 Duo, Core 2 Quad, Atom), Sun Microsystems microprocessor (e.g., SPARC), IBM microprocessor (e.g., IBM 750), Motorola microprocessor (e.g., Motorola 68000), Advanced Micro Devices ("AMD") microprocessor, Texas Instrument microcontroller, and any other microprocessor or microcontroller.

Processing unit 1101 may include a personal computer (PC), such as a Macintosh® (from Apple Inc. of Cupertino, Calif.), Windows®-based PC (from Microsoft Corporation of Redmond, Wash.), or one of a wide variety of hardware platforms that run the UNIX operating system or other operating systems. For at least some embodiments, processing unit 1101 includes a general purpose or specific purpose data processing system based on Intel, AMD, Motorola, IBM, Sun Microsystems, IBM processor families, or any other processor families. As shown in FIG. 11, a memory 1103 is coupled to the processing unit 1101 by a bus 1123. Memory 1103 has instructions and data 1104 stored thereon which when accessed by processing unit 1101 cause the processing unit 1101 to perform methods to provide label free or native particle analysis, as described herein.

Memory 1103 can be dynamic random access memory ("DRAM") and can also include static random access memory ("SRAM"). A bus 1123 couples processing unit 1101 to memory 1103 and also to a non-volatile storage 1109 and to a display controller 1105 (if a display is used) and to an input/output (I/O) controller(s) 1111. Display controller 1105 controls in the conventional manner a display on a display device 1107 which can be a cathode ray tube (CRT), liquid crystal display (LCD), or any other display device. Input/output devices 1117 can include a keyboard, disk drives, printers, a scanner, a camera, and other input and output devices, including a mouse or other pointing device. I/O controller 1111 is coupled to one or more audio input devices 1113 such as, for example, one or more microphones.

Display controller 1105 and 110 controller 1111 can be implemented with conventional well-known technology. An audio output 1115 such as, for example, one or more speakers, may be coupled to I/O controller 1111. Non-volatile storage 1109 is often a magnetic hard disk, an optical disk, or another form of storage for large amounts of data. Some of this data is often written, by a direct memory access process, into memory 1103 during execution of software in data processing system 1100 to perform methods described herein.

One of skilled in the art will immediately recognize that the terms "computer-readable medium" and "machine-readable medium" include any type of storage device that is accessible by processing unit 1101. Data processing system 1100 can interface to external systems through a modem or network interface 1121. It will be appreciated that modem or network interface 1121 can be considered to be part of data processing system 1100. This interface 1121 can be an analog modem, ISDN modem, cable modem, token ring interface, satellite transmission interface, or other interfaces for coupling a data processing system to other data processing systems.

It will be appreciated that data processing system 1100 is one example of many possible data processing systems which have different architectures. For example, personal computers based on an Intel microprocessor often have multiple buses, one of which can be an input/output (I/O) bus for the peripherals and one that directly connects processing unit 1101 and memory 1103 (often referred to as a memory bus). The buses are connected together through bridge components that perform any necessary translation due to differing bus protocols.

Network computers are another type of data processing system that can be used with the embodiments as described herein. Network computers do not usually include a hard disk or other mass storage, and the executable programs are loaded from a network connection into memory 1103 for execution by processing unit 1101. A typical data processing system will usually include at least a processor, memory, and a bus coupling the memory to the processor.

It will also be appreciated that data processing system 1100 can be controlled by operating system software which includes a file management system, such as a disk operating system, which is part of the operating system software. Operating system software can be the family of operating systems known as Macintosh® Operating System (Mac OS®) or Mac OS X® from Apple Inc. of Cupertino, Calif., or the family of operating systems known as Windows® from Microsoft Corporation of Redmond, Wash., and their associated file management systems. The file management system is typically stored in non-volatile storage 1109 and causes processing unit 1101 to execute the various acts required by the operating system to input and output data and to store data in memory, including storing files on non-volatile storage 1109.

In various embodiments, hardwired circuitry may be used in combination with software instructions to implement methods described herein. A non-transitory machine readable medium can be used to store software and data which when executed by a data processing system causes the system to perform various methods described herein. This executable software and data may be stored in various places including for example ROM, volatile RAM, non-volatile memory, and/or cache. Portions of this software and/or data may be stored in any one of these storage devices.

Thus, a machine readable medium includes any mechanism that provides (i.e., stores and/or transmits) information in a form accessible by a machine (e.g., a computer, network device, or any device with a set of one or more processors, etc.). For example, a machine readable medium includes recordable/non-recordable media (e.g., read only memory (ROM); random access memory (RAM); magnetic disk storage media; optical storage media; flash memory devices; and the like.

The methods as described herein can be implemented using dedicated hardware (e.g., using Field Programmable Gate Arrays, or Application Specific Integrated Circuit) or shared circuitry (e.g., microprocessors or microcontrollers) under control of program instructions stored in a machine-readable medium. The methods as described herein can also be implemented as computer instructions for execution on a data processing system, such as system 1100 of FIG. 11.

In the foregoing specification, embodiments of the invention have been described with reference to specific exemplary embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. An apparatus comprising:
a light generating system configured to produce a first set of light pulses in a first wavelength region and a second set of light pulses in a second wavelength region, wherein the first and the second wavelength regions do not substantially overlap, and wherein the light generating system is internally configured to positively chirp the first set of light pulses and negatively chirp the second set of light pulses;
a first optical system coupled to the light generating system, the first optical system comprising optics configured to combine the first set of chirped light pulses and the second set of chirped light pulses into a set of combined light pulses, wherein each of the combined light pulses comprises a first pulse from the first set of chirped light pulses and a second pulse from the second set of chirped light pulses; and
a flow cell coupled to the first optical system and configured to convey, in a flow, particles for analysis, wherein at least one of the particles is exposed to a plurality of the combined light pulses.

2. The apparatus of claim 1, wherein the light generating system comprises temporally dispersive means to positively chirp the first set of light pulses and negatively chirp the second set of light pulses.

3. The apparatus of claim 1, further comprising a synchronization system configured to provide synchronization timing signals to the light generating system, wherein the synchronization timing signals are configured to establish a fixed phase relationship between the first set of light pulses and the second set of light pulses.

4. The apparatus of claim 1, wherein, for each of the combined light pulses, the first pulse from the first set of chirped light pulses is at least partially spatially and temporally overlapping with the second pulse from the second set of chirped light pulses.

5. The apparatus of claim 1, further comprising:
a second optical system coupled to the flow cell, the second optical system configured to collect an interaction light signal resulting from an interaction of the plurality of the combined light pulses with the at least one of the particles; and
an analysis system comprising spectrally dispersive means, the analysis system configured to measure a plurality of spectral components of the interaction light signal.

6. An apparatus comprising:
a light generating system configured to produce a first set of light pulses in a first wavelength region and a second set of light pulses in a second wavelength region, wherein the first and the second wavelength regions do not substantially overlap, and wherein the light generating system is internally configured to positively chirp the first set of light pulses and negatively chirp the second set of light pulses;
a first optical system coupled to the light generating system, the first optical system comprising optics configured to combine the first set of chirped light pulses and the second set of chirped light pulses into a set of combined light pulses, wherein each of the combined light pulses comprises a first pulse from the first set of chirped light pulses and a second pulse from the second set of chirped light pulses; and
a sample holder coupled to the first optical system and configured to hold a sample for analysis, wherein at least a portion of the sample is exposed to a plurality of the combined light pulses.

7. The apparatus of claim 6, wherein the light generating system comprises temporally dispersive means to positively chirp the first set of light pulses and negatively chirp the second set of light pulses.

8. The apparatus of claim 6, further comprising a synchronization system configured to provide synchronization timing signals to the light generating system, wherein the synchronization timing signals are configured to establish a fixed phase relationship between the first set of light pulses and the second set of light pulses.

9. The apparatus of claim 6, wherein, for each of the combined light pulses, the first pulse from the first set of chirped light pulses is at least partially spatially and temporally overlapping with the second pulse from the second set of chirped light pulses.

10. The apparatus of claim 6, further comprising:
a second optical system coupled to the sample holder, the second optical system configured to collect an interaction light signal resulting from an interaction of the plurality of the combined light pulses with the at least a portion of the sample; and
an analysis system comprising spectrally dispersive means, the analysis system configured to measure a plurality of spectral components of the interaction light signal.

11. An apparatus comprising:
a light generating system configured to produce a first set of light pulses in a first wavelength region and a second set of light pulses in a second wavelength region, wherein the first and the second wavelength regions do not substantially overlap, and wherein the light generating system is internally configured to positively chirp the first set of light pulses and negatively chirp the second set of light pulses;
a first optical system coupled to the light generating system, the first optical system comprising optics configured to combine the first set of chirped light pulses and the second set of chirped light pulses into a set of combined light pulses, wherein each of the combined light pulses comprises a first pulse from the first set of chirped light pulses and a second pulse from the second set of chirped light pulses; and
a flow cell coupled to the first optical system and configured to convey, in a flow, particles for analysis, wherein at least one of the particles is exposed to at least one of the combined light pulses.

12. The apparatus of claim 11, wherein the light generating system comprises temporally dispersive means to positively chirp the first set of light pulses and negatively chirp the second set of light pulses.

13. The apparatus of claim 11, further comprising:
a continuous-wave light source optically coupled to the flow cell, the continuous-wave light source configured to convey light to the at least one of the particles;
a photodetector configured to convert an optical signal resulting from an interaction of light from the continuous-wave light source and the at least one of the particles into an electronic detection signal; and
a triggering circuit configured to generate a triggering signal for the light generating system from the electronic detection signal.

14. The apparatus of claim 11, wherein, for each of the combined light pulses, the first pulse from the first set of chirped light pulses is at least partially spatially and temporally overlapping with the second pulse from the second set of chirped light pulses.

15. The apparatus of claim 11, further comprising:
a second optical system coupled to the flow cell, the second optical system configured to collect an interaction light signal resulting from an interaction of the at least one of the combined light pulses with the at least one of the particles; and
an analysis system comprising spectrally dispersive means, the analysis system configured to measure a plurality of spectral components of the interaction light signal.

16. An apparatus comprising:
a light generating system configured to produce a first set of light pulses in a first wavelength region and a second set of light pulses in a second wavelength region, wherein the first and the second wavelength regions do not substantially overlap, and wherein the light generating system is internally configured to positively chirp the first set of light pulses and negatively chirp the second set of light pulses;
a first optical system coupled to the light generating system, the first optical system comprising optics configured to combine the first set of chirped light pulses and the second set of chirped light pulses into a set of combined light pulses, wherein each of the combined light pulses comprises a first pulse from the first set of chirped light pulses and a second pulse from the second set of chirped light pulses; and
a sample holder coupled to the first optical system and configured to hold a sample for analysis, wherein at least a portion of the sample is exposed to at least one of the combined light pulses.

17. The apparatus of claim 16, wherein the light pulses in at least one of the first set and the second set of light pulses are amplified light pulses.

18. The apparatus of claim 16, wherein the light generating system comprises temporally dispersive means to positively chirp the first set of light pulses and negatively chirp the second set of light pulses.

19. The apparatus of claim 16, wherein, for each of the combined light pulses, the first pulse from the first set of chirped light pulses is at least partially spatially and temporally overlapping with the second pulse from the second set of chirped light pulses.

20. The apparatus of claim 16, further comprising:
a second optical system coupled to the sample holder, the second optical system configured to collect an interaction light signal resulting from an interaction of the at least one of the combined light pulses with the at least a portion of the sample; and
an analysis system comprising spectrally dispersive means, the analysis system configured to measure a plurality of spectral components of the interaction light signal.

* * * * *